(12) United States Patent
Berlin et al.

(10) Patent No.: US 10,760,181 B2
(45) Date of Patent: Sep. 1, 2020

(54) CHEMICALLY ENCODED SPATIALLY ADDRESSED LIBRARY SCREENING PLATFORMS

(71) Applicant: City of Hope, Duarte, CA (US)

(72) Inventors: Jacob Berlin, Monrovia, CA (US); Gregory Copeland, Claremont, CA (US); Kathleen Elison, San Bernardino, CA (US); Hurik Muradyan, Glendale, CA (US)

(73) Assignee: City of Hope, Duarte, CA (US)

( * ) Notice: Subject to any disclaimer, the term of this patent is extended or adjusted under 35 U.S.C. 154(b) by 177 days.

(21) Appl. No.: 15/553,140

(22) PCT Filed: Feb. 24, 2016

(86) PCT No.: PCT/US2016/019426
§ 371 (c)(1),
(2) Date: Aug. 23, 2017

(87) PCT Pub. No.: WO2016/138184
PCT Pub. Date: Sep. 1, 2016

(65) Prior Publication Data
US 2018/0245241 A1    Aug. 30, 2018

Related U.S. Application Data

(60) Provisional application No. 62/120,262, filed on Feb. 24, 2015.

(51) Int. Cl.
*C40B 50/16*     (2006.01)
*G01N 33/543*     (2006.01)
(Continued)

(52) U.S. Cl.
CPC .......... *C40B 50/16* (2013.01); *C12N 15/1065* (2013.01); *C40B 40/10* (2013.01);
(Continued)

(58) Field of Classification Search
CPC ........... B82Y 5/00; C40B 40/10; C40B 50/16; C40B 70/00; G01N 33/54313;
(Continued)

(56) References Cited

U.S. PATENT DOCUMENTS

| | | | |
|---|---|---|---|
| 4,672,040 A | 6/1987 | Josephson | |
| 5,034,506 A | 7/1991 | Summerton et al. | |

(Continued)

FOREIGN PATENT DOCUMENTS

| | | |
|---|---|---|
| EP | 1 239 286 A2 | 9/2002 |
| JP | H 08504444 A | 5/1996 |

(Continued)

OTHER PUBLICATIONS

Altschul et al., "Gapped BLAST and PSI-BLAST: a new generation of protein database search programs.," *Nucleic Acids Res.*, 25(17):3389-3402 (1997).

(Continued)

*Primary Examiner* — Jeremy C Flinders
(74) *Attorney, Agent, or Firm* — Arnold & Porter Kaye Scholer

(57) ABSTRACT

Provided herein are encoded split pool libraries useful, inter alia, for forming highly diverse and dense arrays for screening and detection of a variety of molecules.

20 Claims, 17 Drawing Sheets

Specification includes a Sequence Listing.

(51) Int. Cl.
  *C40B 40/10* (2006.01)
  *C40B 70/00* (2006.01)
  *C12N 15/10* (2006.01)
  *B82Y 5/00* (2011.01)

(52) U.S. Cl.
  CPC ....... *C40B 70/00* (2013.01); *G01N 33/54313* (2013.01); *G01N 33/54326* (2013.01); *G01N 33/54346* (2013.01); *G01N 33/54353* (2013.01); *B82Y 5/00* (2013.01)

(58) Field of Classification Search
  CPC ....... G01N 33/54326; G01N 33/54346; G01N 33/54353; C12N 15/1065
  See application file for complete search history.

(56) References Cited

U.S. PATENT DOCUMENTS

| | | |
|---|---|---|
| 5,143,854 A | 9/1992 | Pirrung et al. |
| 5,235,033 A | 8/1993 | Summerton et al. |
| 5,565,324 A | 10/1996 | Still et al. |
| 5,573,905 A | 11/1996 | Lerner et al. |
| 5,770,358 A | 6/1998 | Dower et al. |
| 6,060,596 A | 5/2000 | Lerner et al. |
| 6,110,426 A | 8/2000 | Shalon et al. |
| 6,368,874 B1 | 4/2002 | Gallop et al. |
| 6,824,987 B1 | 11/2004 | Schreiber et al. |
| 6,936,477 B2 | 8/2005 | Still et al. |
| 7,615,368 B1 | 11/2009 | Brown et al. |
| 7,932,213 B2 | 4/2011 | Park et al. |
| 8,039,271 B2 | 10/2011 | Seul |
| 8,795,967 B2 | 8/2014 | Chee et al. |
| 2001/0016316 A1 | 8/2001 | Virtanen |
| 2002/0150909 A1* | 10/2002 | Stuelpnagel ......... B01J 19/0046 435/6.1 |
| 2003/0027221 A1 | 2/2003 | Scott et al. |
| 2003/0134333 A1 | 7/2003 | Dehlinger et al. |
| 2003/0228619 A1 | 12/2003 | Needels |
| 2006/0040286 A1 | 2/2006 | Mirkin et al. |

FOREIGN PATENT DOCUMENTS

| | | |
|---|---|---|
| JP | 2013-500725 A | 1/2013 |
| WO | WO 1994/13623 | 6/1994 |
| WO | WO 1995/12608 A1 | 5/1995 |
| WO | WO 1996/017958 | 6/1996 |
| WO | WO 1996/024061 A1 | 8/1996 |
| WO | WO 1998/20019 A1 | 5/1998 |
| WO | WO 1999/67641 A | 12/1999 |
| WO | WO 2000/71995 A2 | 11/2000 |
| WO | WO 2005/123959 A2 | 12/2005 |
| WO | WO 2007/084192 A2 | 7/2007 |
| WO | WO 2010/093705 A2 | 8/2010 |
| WO | WO 2011/014879 | 2/2011 |
| WO | WO 2011/14583 A1 | 11/2011 |
| WO | WO 2014/026283 A1 | 2/2014 |
| WO | WO 2016/138184 A1 | 9/2016 |

OTHER PUBLICATIONS

Altschul et al., "Basic local alignment search tool," *J. Mol. Biol.*, 215:403-410 (1990).
Ausubel et al., *Current Protocols in Molecular Biology* (1995 Supplement).
Bolli et al., "α-Bicyclo-DNA: Synthesis, Characterization, and Pairing Properties of α-DNA-Analogues with Restricted Conformational Flexibility in the Sugar-Phosphate Backbone," Chapter 7, *Carbohydrate Modifications in Antisense Research* Sanghui & Cook, eds.(1994).
Consensus Information Document, "What you Need to Know about Biosimilar Medicinal Products," *Ref. Ares* (2014).
Czarnik et al., "Encoding Emthods for Combinatorial Chemistry," *Curr. Opin. Chem. Biol.*, 1:60-66 (1997).
Fodor, "Light-Directed, Spatially Addressable Parallel Chemical Synthesis," *Science*, 251(4995):767-773 (1991).
Furka et al., "General method for rapid synthesis of multicomponent peptide mixtures," *Int. J. Pept. Protein Res.*37, 487-493 (1991).
Henikoff et al., "Amino acid substition matrices from protein blocks," *Proc. Nat'l Acad. Sci. USA*, 89:10915-10919 (1992).
Herdewijn et al., "Hexopyranosyl-Like Oligonucleotides," Chapter 6, *Carbohydrate Modifications in Antisense Research* Sanghui & Cook, eds.(1994).
Hogg, "Disulfide bonds as switches for protein function," *Trends in Biochemical Sciences* 28(4):210-214 (2003).
Hughes et al., "Expression profiling using microarrays fabricated by an ink-jet oligonucleotide synthesizer," *Nat. Biotech.*, 4:342-347 (2001).
International Search Report in International Application No. PCT/US2016/19426 dated May 20, 2016.
Johnston, "Gene Chips: Array of hope for understanding gene regulation," *Curr. Biol.* 8: R171-R174 (1998).
Karlin et al., "Applications and statistics for multiple high-scoring segments in colecular sequences," *Proc. Nat'l Acad. Sci. USA*, 90(12):5873-5787 (1993).
Karlin et al., "Applications and statistics for multiple high-scoring segments in molecular sequences," *Proc. Natl. Acad. Sci. USA* 90:5873-5787 (1993).
Kohler et al., "Continuous cultures of fused cells secreting antibody of predefined specificity," *Nature* 256:495-497 (1975).
Kozbor et al., "The production of monoclonal antibodies from human lymphocytes," *Immunology Today* 4(3):72-79 (1983).
Lam et al., "A new type of synthetic peptide library for identifying ligand-binding activity," *Nature* 354: 82-84 (1991).
Lybecker, "The Biologics Revolution in the Production of Drugs," *Fraser Institute* (2016).
Marks et al., "By-Passing Immunization: Building High Affinity Human Antibodies by Chain Shuffling," *Biotechnology* 10:779-783 (1992).
McCafferty et al., "Phage antibodies: filamentous phage displaying antibody variable domains," *Nature* 348:552-554 (1990).
Needleman et al., "A General Method Applicable to the Search for Similarities in the Amino Acid Sequence of Two Proteins," *J. Mol. Biol.* 48(3):443-453 (1970).
Office Action dated Sep. 20, 2019 in European Appln. 16756316.2.
Pearson et al., "Improved tools for biological sequence comparison," *Proc. Nat'l. Acad. Sci. USA* 85:2444-2448 (1988).
Ramon-Azcon et al., "Sensitive and Spatially Multiplexed Detection System Based on Dielectrophoretic Manipulation of DNA-Encoded Particles Used as Immunoreactions Platform," *Analytical Chemistry*, 83(3):1053-1060 (2011).
Roder et al., "Recent Advances in the EBV—Hybridoma Technique," Abstract 106 from Symposium, *Monoclonal Antibodies and Cancer Therapy* (1985).
Sambrook et al., "Detection and Analysis of Proteins Expressed from Cloned Genes," *Molecular Cloning: A Laboratory Manual*, 18.1-18.88 (1989).
Schummer et al., "Inexpensive Handheld Device for the Construction of High-Density Nucleic Acid Arrays," *BioTechniques* 23: 1087-1092 (1997).
Smith et al., "Comparison of Biosequences," *Adv. Appl. Math.* 2:482c (1970).
Supplementary Partial European Search Report dated Oct. 23, 2018 in European Appln. No. 16756316.2.
Zhi et al., "Multianalyte Immunoassay with Self-Assembled Addressable Microparticle Array on a Chip," *Analytical Biochemistry*, 318(2):236-243 (2003).
Office Action dated Dec. 3, 2019 in Japanese Appln. 2017-562972 with translation.
Office Action dated Feb. 5, 2020 in Australian Appln. 2016222755.
Anonymous et al., "Enterprise and Industry Process on Corporate Responsibility in the Field of Pharmaceuticals Access to Medicines in Europe What You Need to Know About," Retrieved from the Internet: URL:http//www.medicinesforeurope.com/wp-content/uploads/2016/03/biosimilars_report_en.pdf (2013).
Extended European Search Report dated Apr. 17, 2020 in European Application No. 19196007.9.

(56) References Cited

OTHER PUBLICATIONS

Office Action dated Jan. 13, 2020 in European Appln No. 19196007.9.
Office Action dated Jan. 14, 2020 in European Appln. No. 19196019.4.
Office Action dated Apr. 9, 2020 in European Appln. 16756316.2.
Extended European Search Report dated Apr. 17, 2020 in European Application No. 19196019.4.

* cited by examiner

Preferred Ranges:

X = 0.1 to 100 nanomoles/mg

1% X ≤ A ≤ 20% X

40% X ≤ B ≤ 99% X

0 % X ≤ C ≤ 50% X

X = 
A) library molecule attachment point
OR
B) encoding tag attachment point
OR
C) core immobilization point Library spatially immobilized as
disordered array via covalent attachment Library spatially immobilized
into an ordered array via
non covalent interactions/self assembly

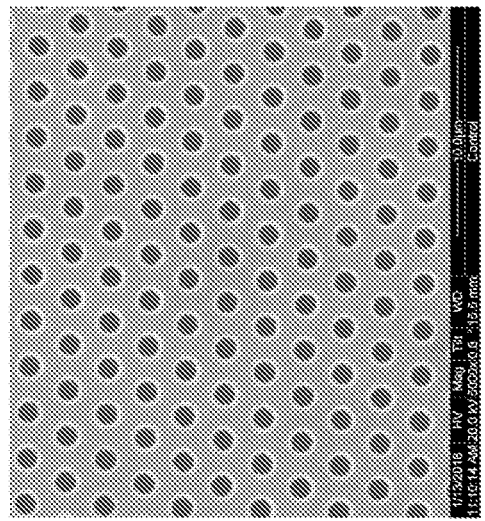
FIG. 16B
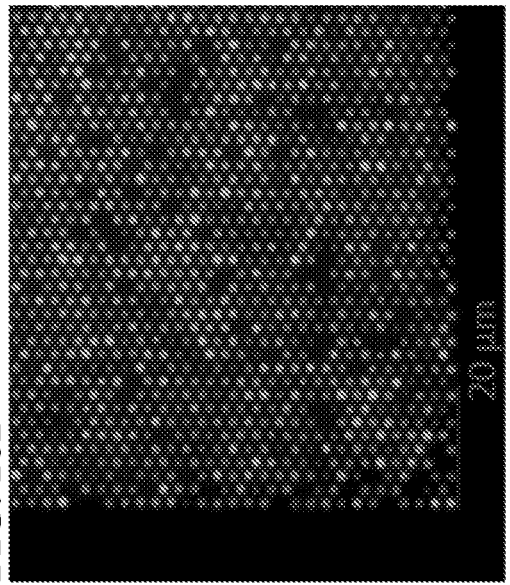
FIG. 16D
FIG. 16A
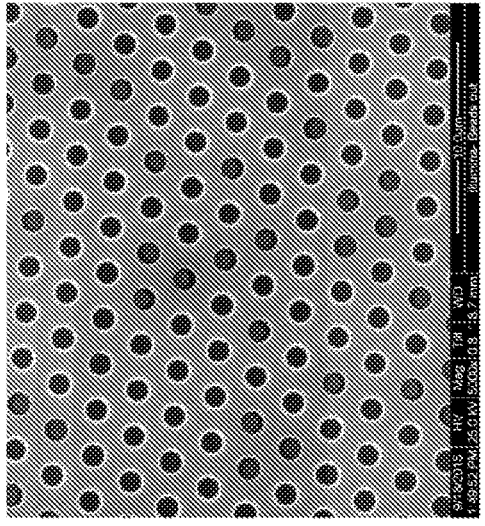
FIG. 16AC

SEQUENCE LISTING

```
<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with hexynyl
<220> FEATURE:
<221> NAME/KEY: misc_feature
<222> LOCATION: (18)..(18)
<223> OTHER INFORMATION: Terminal modified with AmMO

<400> SEQUENCE: 1
aaccacacac acacaacc                                                 18

<210> SEQ ID NO 2
```

```
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with hexynyl
<220> FEATURE:
<221> NAME/KEY: misc_feature
<222> LOCATION: (18)..(18)
<223> OTHER INFORMATION: Terminal modified with AmMO

<400> SEQUENCE: 2
aaccacacac accaaacc                                               18

<210> SEQ ID NO 3
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with hexynyl
<220> FEATURE:
<221> NAME/KEY: misc_feature
<222> LOCATION: (18)..(18)
<223> OTHER INFORMATION: Terminal modified with AmMO

<400> SEQUENCE: 3
acgaacacac acgtacga                                               18

<210> SEQ ID NO 4
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with hexynyl
<220> FEATURE:
<221> NAME/KEY: misc_feature
<222> LOCATION: (18)..(18)
<223> OTHER INFORMATION: Terminal modified with AmMO

<400> SEQUENCE: 4
caagacacac acgtcaag                                               18

<210> SEQ ID NO 5
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with hexynyl
<220> FEATURE:
<221> NAME/KEY: misc_feature
<222> LOCATION: (18)..(18)
<223> OTHER INFORMATION: Terminal modified with AmMO

<400> SEQUENCE: 5
ccttacacac acgtcctt                                               18
```

-continued

```
<210> SEQ ID NO 6
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with hexynyl
<220> FEATURE:
<221> NAME/KEY: misc_feature
<222> LOCATION: (18)..(18)
<223> OTHER INFORMATION: Terminal modified with AmMO

<400> SEQUENCE: 6
acgaacacac actgacga                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with hexynyl
<220> FEATURE:
<221> NAME/KEY: misc_feature
<222> LOCATION: (18)..(18)
<223> OTHER INFORMATION: Terminal modified with AmMO

<400> SEQUENCE: 7
caagacacac actgcaag                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with hexynyl
<220> FEATURE:
<221> NAME/KEY: misc_feature
<222> LOCATION: (18)..(18)
<223> OTHER INFORMATION: Terminal modified with AmMO

<400> SEQUENCE: 8
ccttacacac actgcctt                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with Cy3

<400> SEQUENCE: 9
tcgtacgtgt gtgttcgt                                                 18

<210> SEQ ID NO 10
<211> LENGTH: 18
<212> TYPE: DNA
```

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with Cy3

<400> SEQUENCE: 10
cttgacgtgt gtgtcttg                                                   18

<210> SEQ ID NO 11
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with Cy3

<400> SEQUENCE: 11
aaggacgtgt gtgtaagg                                                   18

<210> SEQ ID NO 12
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with Alex647

<400> SEQUENCE: 12
tcgtcagtgt gtgttcgt                                                   18

<210> SEQ ID NO 13
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with 6-FAM

<400> SEQUENCE: 13
cttgcagtgt gtgtcttg                                                   18

<210> SEQ ID NO 14
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with 6-FAM

<400> SEQUENCE: 14
aaggcagtgt gtgtaagg                                                   18

<210> SEQ ID NO 15
<211> LENGTH: 18
```

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with Cy3

<400> SEQUENCE: 15
ggttgtgtgt gtgtggtt                                              18

<210> SEQ ID NO 16
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Terminal modified with 6-FAM

<400> SEQUENCE: 16
ggtttggtgt gtgtggtt                                              18

<210> SEQ ID NO 17
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 17

Tyr Pro Tyr Asp Val Pro Asp Tyr Ala
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 18

Glu Gln Lys Leu Ile Ser Glu Glu Asp Leu
1               5                   10
```

CHEMICALLY ENCODED SPATIALLY ADDRESSED LIBRARY SCREENING PLATFORMS

CROSS REFERENCE TO RELATED APPLICATIONS

This application claims the benefit of U.S. Provisional Application No. 62/120,262, filed Feb. 24, 2015, the content of which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48440-511001WO_ST25, created Feb. 24, 2016, 5,967 bytes, machine format IBM-PC, MS Windows operating system, is hereby incorporated by reference.

BACKGROUND OF THE INVENTION

The number of molecules displayed by arrays used for screening and detection methods is restricted by the synthetic method of the array. In theory, split pool synthesis can generate enormous libraries—limited only by the number of chemical steps and number of unique building blocks utilized per step (i.e. a 5 step library utilizing 100 unique building blocks per step would in theory yield a $100^5$ or 10 billion member chemical library). However, in practice, encoded split pool strategies face numerous practical constraints. Libraries that are decodable but not screenable or vice versa are not useful. The encoding strategy may be practically limited in the number and type of chemical steps or building blocks used. An encoded split pool library platform which requires large particles for decoding (e.g., by radio frequency tags or mass spectrometry) will normally need to contain fewer library members than a similar library that can be created on smaller particles. If assays are to be performed on a particle, the ligand density on each particle and the surface chemistry environment around each ligand should not interfere with the assay. The serial nature of reported decoding strategies also limits the number of "hits" which can be identified in a cost effective manner in a given screen, and therefore can limit the size of a library that is screened. The present invention addresses these and other problems in the art.

BRIEF SUMMARY OF THE INVENTION

In one aspect, a microparticle is provided. The microparticle is covalently attached to a ligand domain through a first linker; and a nucleic acid domain through a second linker, wherein the second linker is cleavable and the first linker is not cleavable under a condition that the second linker is cleavable.

In another aspect, a solid support attached to a microparticle is provided, wherein the microparticle is covalently attached to (i) a ligand domain through a first linker; and (ii) a cleaved linker moiety.

In another aspect, a method of forming a cleaved microparticle is provided. The method includes attaching a microparticle as provided herein including embodiments thereof to a solid support, thereby forming an immobilized microparticle. The second linker of the immobilized microparticle is cleaved, thereby forming a cleaved microparticle.

In another aspect, a method of detecting a ligand binder is provided. The method includes (i) attaching a microparticle as provided herein including embodiments thereof to a solid support, thereby forming an immobilized microparticle. (ii) A complementary nucleic acid is bound to the nucleic acid domain of the immobilized microparticle and a location of the nucleic acid domain on the solid support is determined, thereby forming a decoded and mapped microparticle. (iii) The second linker of the decoded and mapped microparticle is cleaved, thereby forming a mapped and cleaved microparticle. (vi) A ligand binder is bound to the ligand domain of the mapped and cleaved microparticle; and (v) a location of the bound ligand binder on the solid support is identified, thereby detecting the ligand binder.

In another aspect, a method of detecting a ligand binder is provided. The method includes (i) contacting a ligand binder with a microparticle as provided herein including embodiments thereof thereby forming a bound ligand binder. (ii) A location of the bound ligand binder is identified on the solid support, thereby detecting the ligand binder.

BRIEF DESCRIPTION OF THE DRAWINGS

In FIG. 9A, a brightfield image of a portion of Applicants' microparticles covalently immobilized to an activated carboxymethyldextran coated slide through amide bond formation. In FIG. 9B on right, an SEM image of a portion of Applicants' microparticles noncovalently immobilized within a custom microfabricated silicon wafer.

FIG. 15A shows SEM of the 0.88 µm Promag particles. FIG. 15B shows a Silicon chip with 1.3 µm center to center spacing of wells in a hexagonal pattern. FIG. 15C shows a Silicon chip with 1.3 µm center to center spacing of wells in a square pattern. FIG. 15D shows a Silicon chip with 1.3 µm center to center spacing of wells in a square pattern-partially filled with microspheres. FIG. 15E shows a Silicon chip with 1.3 µm center to center spacing of wells in a hexagonal pattern, filled with microspheres. FIG. 15F shows a Silicon chip with 1.3 µm center to center spacing of wells in a hexagonal pattern, filled with microspheres-tilted. FIG. 15G shows a fluorescent Image of Alexafluor 488-labeled microspheres immobilized in partially filled silicon chip with 1.3 µm center to center spacing of wells in a hexagonal pattern. FIG. 15H shows a bright field image of microspheres immobilized in a partially filled quartz chip with 1.3 µm center to center spacing of wells in a hexagonal pattern.

FIG. 16A, FIG. 16B, FIG. 16C, and FIG. 16D: FIG. 16A shows autofluorescence of microspheres immobilized in a partially filled quartz chip with 1.3 µm center to center spacing of wells in a hexagonal pattern. FIG. 16B shows a Silicon chip with 2.4 µm center to center spacing of wells in a hexagonal pattern. FIG. 16AC shows a Silicon chip with 2.4 µm center to center spacing of wells in a hexagonal pattern, partially filled with microspheres. FIG. 16D shows a fluorescent image of DNA tagged-microspheres hybridized with fluorescently labeled DNA complements immobilized in a silicon chip. The chip is partially filled and has 2.4 µm center to center spacing of wells in a hexagonal pattern.

DETAILED DESCRIPTION OF THE INVENTION

Definitions

Figure 1:
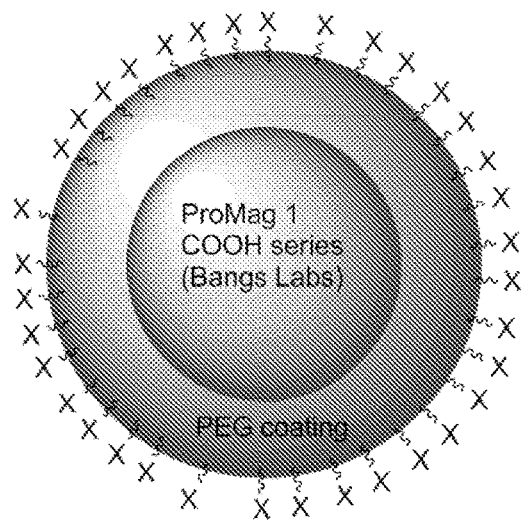
FIG. 1: Schematic illustrating general structure of microparticles used to create library. Variation in ratios of A, B, and C are achieved through one or more synthetic transformations applied to the starting material ProMag 1 COOH series particles. Initial target ratios are set by relative ratios of mixtures of building blocks used to assemble the particle surface. The final ratios achieved are measured through a combination of TGA, LC/MS or gel analysis of cleaved products, and colorimetric or fluorescence based solid phase assays. Preferred ranges: X has a concentration of 0.1 to 100 nanomoles/mg; 1% X≤A≤20% X; 40% X≤B≤99% X; 0% X≤C≤50% X; wherein X is A (library molecule attachment point), B (encoding tag attachment point) or C (core immobilization point).
Figure 2:
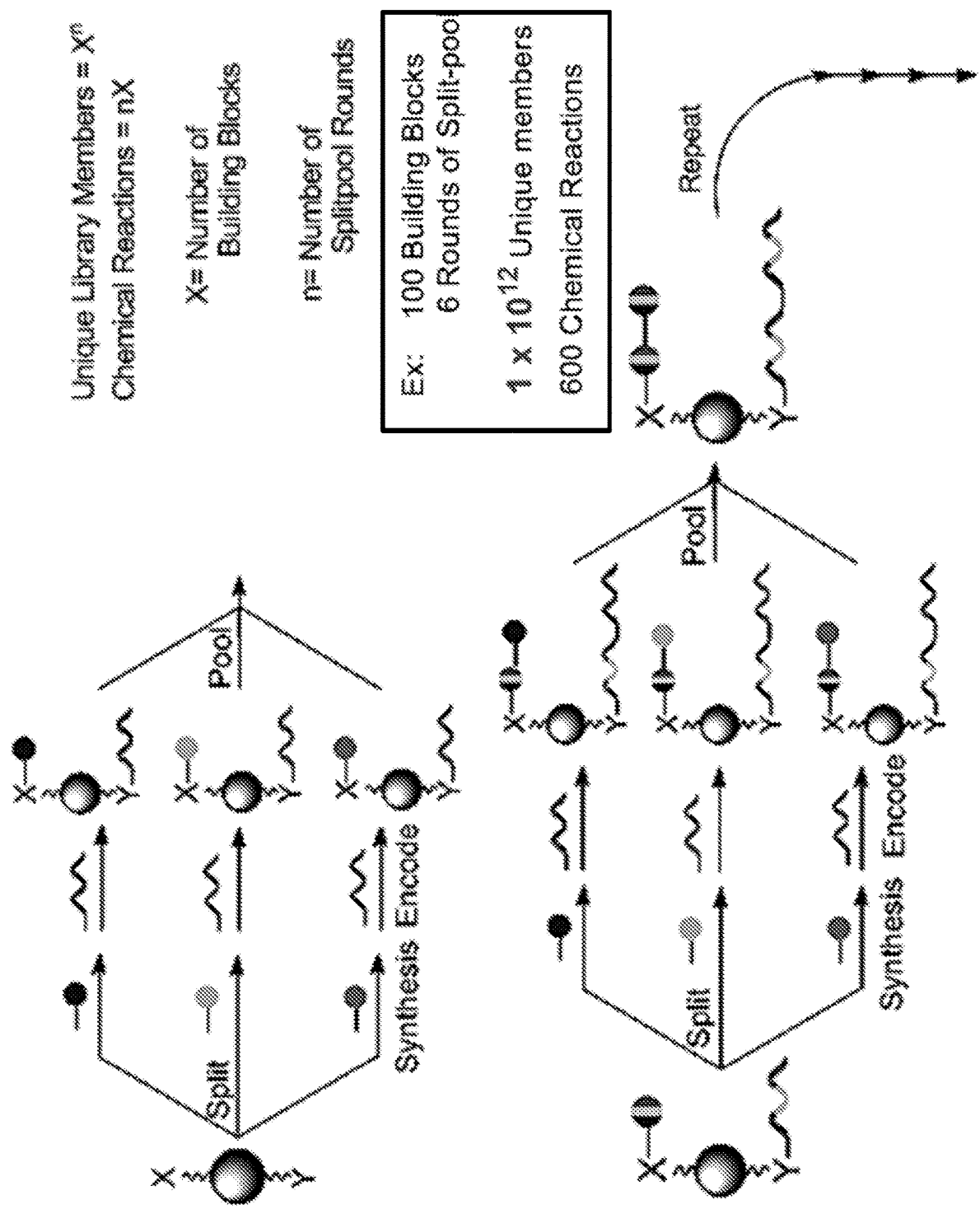
FIG. 2: General schematic for how encoded, split pool synthesis can be performed; emphasizing the exponential increase in chemical diversity observed with a linear increase in the number of chemical steps and building blocks. For a general review, see: Czarnik, A. W. "Encoding methods for combinatorial chemistry," Curr. Opin. Chem. Biol. 1997, 1, 60-66. Example: 100 building blockes, 6 rounds of split-pool, $1\times10^{12}$ unique members, 600 chemical reactions. n is the number of splitpool rounds, x is the number of building blockes, unique library memebers=$X^n$, chemical reactions=$n^x$

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH₂—NH—OCH₃ and —CH₂—O—Si(CH₃)₃. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R'', —OR', —SR', and/or —SO₂R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C₁-C₄)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R, —C(O)R', —$CO_2$R, —CONR'R", —OC(O)NR'R", —NR"C(O)W, —NR'—C(O)NR"R'", —NR"C($O_2$)R', —NR—C(NR'R")=NR'", —S(O)R', —S($O)_2$R', —S($O)_2$N(R)('R"—NRS$O_2$R'), —CN, and —$NO_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R, —C(O)R', —$CO_2$R, —CONR'R", —OC(O)NR'R", —NR"C(O)W, —NR'—C(O)NR"R'", NR"C($O)_2$R', NRC(NR'R")=NR'", S(O)R', —S($O)_2$R', —S($O)_2$N(R')(R", —NRS$O_2$R'), —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{1A}$-substituted or unsubstituted alkyl, a plurality of $R^{1A}$ substituents may be attached to the alkyl moiety wherein each RVA substituent is optionally different. Where an R-substituted moiety is substituted with a plurality R substituents, each of the R-substituents may be differentiated herein using a prime symbol (') such as R', R", etc. For example, where a moiety is $R^{1A}$-substituted or unsubstituted alkyl, and the moiety is substituted with a plurality of $R^{1A}$ substituents, the plurality of $R^{1A}$ substituents may be differentiated as $R^{1A'}$, $R^{1A''}$, $R^{1A'''}$, etc. In some embodiments, the plurality of R substituents is 3. In some embodiments, the plurality of R substituents is 2.

In embodiments, a compound as described herein may include multiple instances of $R^1$, $R^2$, $R^3$, $R^4$, $R^5$, $R^6$, $R^{6A}$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, and/or other substituents and variables. In such embodiments, each variable may optional be different and be appropriately labeled to distinguish each group for greater clarity. For example, where each $R^{6A}$ is different, they may be referred to, for example, as $R^{6A.1}$, $R^{6A.2}$, $R^{6A.3}$, or $R^{6A.4}$, respectively, wherein the definition of $R^{6A}$ is assumed by $R^{6A.1}$, $R^{6A.2}$, $R^{6A.3}$, and/or $R^{6A.4}$. The variables used within a definition of $R^1$, $R^2$, $R^3$, $R^4$, $R^5$, $R^6$, $R^{6A}$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, and/or other variables that appear at multiple instances and are different may similarly be appropriately labeled to distinguish each group for greater clarity.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where variables s and d are independently integers of from 0 to 3, and X is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The symbol "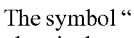" denotes the point of attachment of a chemical moiety to the remainder of a molecule or chemical formula.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g. mRNA) or altering transcript splicing (e.g. single stranded morpholino oligo).

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the nucleic acid domain includes a detectable label, as disclosed herein and generally known in the art.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

Nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the microparticle is non-covalently attached to a solid support through a non-covalent chemical reaction between a component of the microparticle and a component of the solid support. In other embodiments, the microparticle includes one or more reactive moieties, e.g., a covalent reactive moiety, as described herein (e.g., an amine reactive moiety). In other embodiments, the microparticle includes a linker with one or more reactive moieties, e.g., a covalent reactive moiety, as described herein (e.g., an amine reactive moiety).

Useful reactive moieties or reactive functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard reactive moieties useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

The reactive moieties can be chosen such that they do not participate in, or interfere with, the chemical stability of the proteins or nucleic acids described herein. By way of example, the nucleic acids can include a vinyl sulfone or other reactive moiety (e.g., maleimide). Optionally, the nucleic acids can include a reactive moiety having the formula S—S—R. R can be, for example, a protecting moiety. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

An example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a ligand domain as described herein and a ligand binder. In embodiments contacting includes, for example, allowing a ligand domain as described herein to interact with a ligand binder.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$—$C_{H1}$ by a disulfide bond. The F(ab)'2 may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)).

"Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

A "solid support" as provided herein refers to any material that can be modified to contain discrete individual sites appropriate for the attachment or association of a microparticle as provided herein including embodiments thereof and is amenable to the methods provided herein including embodiments thereof. Examples of solid supports include without limitation, glass and modified or functionalized glass (e.g., carboxymethyldextran functionalized glass), plastics (including acrylics, polystyrene and copolymers of styrene and other materials, polypropylene, polyethylene, polybutylene, polyurethanes, Teflon™, etc.), polysaccharides, nylon or nitrocellulose, composite materials, ceramics, and plastic resins, silica or silica-based materials including silicon and modified silicon (e.g., patterned silicon), carbon, metals, quartz (e.g., patterned quartz), inorganic glasses, plastics, optical fiber bundles, and a variety of other polymers. In general, the substrates allow optical detection and do not appreciably fluoresce.

The solid support provided herein including embodiments thereof may form part of an ion-sensitive field-effect transistor (ISFET) microarray. The solid support may be planar (e.g., flat planar substrates such as glass, polystyrene and other plastics and acrylics). Although it will be appreciated by a person of ordinary skill in the art that other configurations of solid supports may be used as well, for example, three dimensional configurations can be used. The solid support may be modified to contain discrete, individual sites (also referred to herein as "wells") for microparticle binding. These sites generally include physically altered sites, i.e. physical configurations such as wells or small depressions in the substrate that can retain the microparticles. The wells may be formed using a variety of techniques well known in the art, including, but not limited to, photolithography, stamping techniques, molding techniques and microetching techniques. It will be appreciated by a person of ordinary skill in the art that the technique used will depend on the composition and shape of the solid support. In embodiments, physical alterations are made in a surface of the solid support to produce wells. The required depth of the wells will depend on the size of the microparticle to be added to the well.

A "microparticle" as used herein refers to a non-planar (e.g. spherical) particle having a size sufficient to attach molecules (e.g., a first, a second or a third linker provided, a ligand domain and a nucleic acid domain), directly or indirectly, through either covalent or non-covalent bonds. The microparticle may include any material that is capable of providing physical support for the molecules (e.g., a first, a second or a third linker provided, a ligand domain and a nucleic acid domain) that are attached to the surface. The material is generally capable of enduring conditions related to the attachment of the molecules (e.g., a first, a second or a third linker provided, a ligand domain and a nucleic acid domain) to the surface and any subsequent treatment, handling, or processing encountered during the performance of an assay. The materials may be naturally occurring, synthetic, or a modification of a naturally occurring material. Suitable microparticle materials may include silicon, ceramics, plastics (including polymers such as, e.g., poly(vinyl chloride), cyclo-olefin copolymers, agarose, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold or silver, copper or aluminum surfaces, magnetic surfaces, e.g. Fe, Mn, Ni, Co, and their oxides, quantum dots, e.g., III-V (GaN, GaP, GaAs, InP, or InAs) or II-VI (ZnO, ZnS, CdS, CdSe, or CdTe) semiconductors, or Ln-doped fluoride nanocrystals, rare earth-doped oxidic nanomaterials either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads, crosslinked beaded Sepharose® or agarose resins, or copolymers of crosslinked bis-acrylamide and azalactone. Other beads include polymer beads, solid core beads, paramagnetic beads, or microbeads. Any other materials known in the art that are capable of having one or more moieties, such as any of an amino, carboxyl, thiol, or hydroxyl reactive moiety, for example, incorporated on its surface, are also contemplated. In embodiments, the microparticle is a magnetic polymer-based sphere. In embodiments, the microparticle is a ProMag™ microsphere. In embodiments, the longest dimension of the microparticle is less than 1000 μm.

Compositions

The compositions provided herein are, inter alia, useful for the assembly of highly dense arrays suitable for a variety of high throughput screening methods. The microparticles provided herein include a ligand domain attached through a first linker and a nucleic acid domain attached through a second linker. By binding to a solid support the microparticles provided herein including embodiments thereof may form part of an array. The ligand domain and the nucleic acid domain are synthesized on the microparticle using methods of encoded split pool chemistry. Encoded split pool chemistry is a method well known in the art and described, inter alia, by the following references: Furka, A.; et al. Int. J. Pept. Protein Res. 1991, 37, 487-493; Kit Lam et al., Nature, 1991; 354: 82-84; U.S. Pat. Nos. 6,060,596; 5,770,358; 6,368,874; 5,565,324; 6,936,477 and 5,573,905; which are all incorporated by reference herein in their entirety and for all purposes. Each step of the ligand domain synthesis (e.g., peptide or chemical compound synthesis) is encoded in the nucleic acid domain by a short nucleic acid sequence serving as an identification bar code. Therefore, each microparticle includes a unique ligand domain and a corresponding nucleic acid domain encoding specific nucleic acid sequences. The specific nucleic acid sequences correspond to the building blocks of the ligand domain and the order in which they were incorporated in the ligand domain. Upon hybridization of a complementary nucleic acid to said nucleic acid domain, the composition of the ligand domain and its location on the array can be determined (decoded). After the identity of the ligand domain and its location on the array have been determined, the nucleic acid domain is removed, the ligand domain may be further modified and contacted with a ligand binder (e.g., biomolecule).

In one aspect, a microparticle is provided. The microparticle is covalently attached to a ligand domain through a first linker; and a nucleic acid domain through a second linker, wherein the second linker is cleavable and the first linker is not cleavable under a condition that the second linker is cleavable.

In embodiments, the microparticle is a microbead. A "microbead" as referred to herein is a polymer-based microparticle of roughly spherical shape with a diameter of about 0.5 μm to about 500 μm. The term "polymer-based" or "polymeric" as provided herein refers to a microparticle or microbead including at least one polymer compound (e.g., polyethylene glycols, polyethylene imides, polysaccharides, polypeptides, or polynucleotides). In embodiments, the microbead is a ProMag™ microsphere. In embodiments, the microbead is a polymer-based magnetic microbead.

The microparticle provided herein including embodiments thereof may be less than 200 μm. Where the microparticle is less than 200 μm a person of ordinary skill in the art will immediately recognize that the longest dimension (e.g. diameter or length) of a microparticle is smaller than 200 μm. In other embodiments, the microparticle is about 20 nm. In some embodiments, the microparticle is from about 0.01 μm to about 200 μm, from about 0.02 μm to about 200 μm, from about 0.05 μm to about 200 μm, from about 0.1 μm to about 200 μm, from about 0.5 μm to about 200 μm, from about 1 μm to about 200 μm, from about 2 μm to about 200 μm, from about 5 μm to about 200 μm, from about 10 μm to about 200 μm, from about 15 μm to about 200 μm, from about 20 μm to about 200 μm, from about 25 μm to about 200 μm, from about 30 μm to about 200 μm, from about 35 μm to about 200 μm, from about 40 μm to about 200 μm, from about 45 μm to about 200 μm, from about 50 μm to about 200 μm, from about 55 μm to about 200 μm, from about 60 μm to about 200 μm, from about 65 μm to about 200 μm, from about 70 μm to about 200 μm, from about 75 μm to about 200 μm, from about 80 μm to about 200 μm, from about 85 μm to about 200 μm, from about 90 μm to about 200 μm, from about 95 μm to about 200 μm, from about 100 μm to about 200 μm, from about 101 μm to about 200 μm, from about 102 μm to about 200 μm, from about 105 μm to about 200 μm, from about 10 μm to about 200 μm, from about 115 μm to about 200 μm, from about 120 μm to about 200 μm, from about 125 μm to about 200 μm, from about 130 μm to about 200 μm, from about 135 μm to about 200 μm, from about 140 μm to about 200 μm, from about 145 μm to about 200 μm, from about 150 μm to about 200 μm, from about 155 μm to about 200 μm, from about 160 μm to about 200 μm, from about 165 μm to about 200 μm, from about 170 μm to about 200 μm, from about 175 μm to about 200 μm, from about 180 μm to about 200 μm, from about 185 μm to about 200 μm, from about 190 μm to about 200 μm, or from about 195 μm to about 200 μm.

In some embodiments, the microparticle is from about 0.01 μm to about 100 μm, from about 0.02 μm to about 100 μm, from about 0.05 μm to about 100 μm, from about 0.1 μm to about 100 μm, from about 0.5 μm to about 100 μm, from about 1 μm to about 100 μm, from about 2 μm to about 100 μm, from about 5 μm to about 100 μm, from about 10 μm to about 100 μm, from about 15 μm to about 100 μm, from about 20 μm to about 100 μm, from about 25 μm to about 100 μm, from about 30 μm to about 100 μm, from about 35 μm to about 100 μm, from about 40 μm to about 100 μm, from about 45 μm to about 100 μm, from about 50 μm to about 100 μm, from about 55 μm to about 100 μm, from about 60 μm to about 100 μm, from about 65 μm to about 100 μm, from about 70 μm to about 100 μm, from about 75 μm to about 100 μm, from about 80 μm to about 100 μm, from about 85 μm to about 100 μm, from about 90 μm to about 100 μm, or from about 95 μm to about 100 μm.

In some embodiments, the microparticle is from about 0.01 µm to about 50 µm, from about 0.02 µm to about 50 µm, from about 0.05 µm to about 50 µm, from about 0.1 µm to about 50 µm, from about 0.5 µm to about 50 µm, from about 1 µm to about 50 µm, from about 2 µm to about 50 µm, from about 5 µm to about 50 µm, from about 10 µm to about 50 µm, from about 15 µm to about 50 µm, from about 20 µm to about 50 µm, from about 25 µm to about 50 µm, from about 30 µm to about 50 µm, from about 35 µm to about 50 µm, from about 40 µm to about 50 µm, or from about 45 µm to about 50 µm.

In some embodiments, the microparticle is from about 0.01 µm to about 20 µm, from about 0.02 µm to about 20 µm, from about 0.05 µm to about 20 µm, from about 0.1 µm to about 20 µm, from about 0.5 µm to about 20 µm, from about 1 µm to about 20 µm, from about 2 µm to about 20 µm, from about 5 µm to about 20 µm, from about 10 µm to about 20 µm, or from about 15 µm to about 20 µm.

In some embodiments, the microparticle is from about 0.01 µm to about 10 µm, from about 0.02 µm to about 10 µm, from about 0.05 µm to about 10 µm, from about 0.1 µm to about 10 µm, from about 0.2 µm to about 10 µm, from about 0.3 µm to about 10 µm, from about 0.4 µm to about 10 µm, from about 0.5 µm to about 10 µm, from about 0.6 µm to about 10 µm, from about 0.7 µm to about 10 µm, from about 0.8 µm to about 10 µm, from about 0.9 µm to about 10 µm, from about 1 µm to about 10 µm, from about 2 µm to about 10 µm or from about 5 µm to about 10 µm.

In embodiments, the microparticle is about 0.9 µm. In embodiments, the microparticle has a diameter of about 0.9 µm. In embodiments, the microparticle is about 0.01, 0.02, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 µm. In other embodiments, the microparticle has a diameter of about 0.01, 0.02, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 µm. The numerical values above represent the size of the microparticle in µm.

In embodiments, the microparticle is a functionalized microbead. Where the microparticle is a functionalized microbead, the microparticle may include any reactive moiety suitable for the conjugate chemistries described herein. The term "functionalized" as provided herein refers to a compound or domain (e.g., microparticle, linker, ligand domain, nucleic acid domain, nucleic acid sequence) including a reactive moiety or reactive functional groups used for conjugate chemistries as described herein. For example, a functionalized microbead may include one or more reactive moieties, such as any of an amino, carboxyl, thiol, or hydroxyl reactive moiety, incorporated on its surface. In embodiments, a first functionalized group allows for attachment of the ligand domain through a first linker. In embodiments, a second functionalized group allows for attachment of the nucleic acid domain through a second linker. In embodiments, the first and the second functionalized group are independently different. Therefore, the ligand domain may be attached to the microparticle through a first linker by conjugation to a different functionalized group than the nucleic acid domain. In embodiments, a third functionalized group connects the microparticle to a solid support. Therefore, in embodiments the microparticle is covalently attached to a solid support.

The microparticle provided herein may include a polymer. In such a case the polymers will carry the reactive moieties to be activated. The polymer may be selected from any suitable class of compounds, for example, polyethylene glycols, polyethylene imides, polysaccharides, polypeptides, or polynucleotides. In embodiments, the microparticle includes bis-amino polyethyleneglycol 3000 and hydroxyl-polyethylene glycol 3000. In embodiments, the microparticle includes a polymer layer. Attachment of the polymers to the microparticle may be effected by a variety of methods which are readily apparent to a person skilled in the art. For example, polymers bearing trichlorosilyl or trisalkoxy groups may be reacted with hydroxyl groups on the microparticle to form siloxane bonds. Attachment to a gold or silver microparticle may take place via thiol groups on the polymer. Alternatively, the polymer may be attached via an intermediate species, such as a self-assembled monolayer of alkanethiols. The type of polymers selected, and the method selected for attaching the polymers to the microparticle, will thus depend on the polymer having suitable reactivity for being attached to the microparticle surface, and on the properties of the polymers regarding non-specific adsorption to, especially, DNA or peptides. The reactive moieties may be present on the polymer or may be added to the polymer by the addition of single or multiple reactive moieties. Optionally, a spacer arm (e.g., linker) can be used to provide flexibility to the binding nucleic acid domain or ligand domain allowing it to interact with its environment in a way which minimizes steric hindrance with the microparticle.

In embodiments, the functionalized microbead is a magnetic polymer-based (polymeric) microbead. In embodiments, the microbead is a ProMag™ microsphere. In embodiments, the microbead includes more than one polymer. In embodiments, the microbead includes a first polymer and a second polymer, wherein the first polymer and the second polymer are chemically different. In embodiments, the first polymer is bis-amino polyethyleneglycol 3000 and the second polymer is hydroxyl-polyethylene glycol 3000. In embodiments, the first polymer includes a first reactive moiety and the second polymer includes a second reactive moiety. A reactive moiety as referred to herein includes any of the functional moieties useful for conjugate chemistry as described herein. In embodiments, the first reactive moiety is an amino functional group and the second reactive moiety is a hydroxyl functional group. In embodiments, the hydroxyl functional group is reacted to form an azidoactate moiety. In embodiments, the first reactive moiety (e.g., amino functional group) is reacted with a reactive moiety (e.g., a carboxyl functional group) of the first linker. In embodiments, the azidoacetate moiety is reacted with a reactive moiety (e.g., an alkynyl functional group) of the second linker.

In embodiments, the microparticle is a polymeric microbead. In embodiments, the microparticle is a dendrimer. A "dendrimer" as referred to herein is a spherical polymeric molecule made from two monomers (e.g., acrylic acid and a diamine). Dendrimers are precisely defined chemical structures that consist of a series of chemical shells built on a small core molecule. Each shell consists of two chemicals, always in the same order. In embodiments, the microparticle is a branched polymer. In embodiments, the microparticle is a magnetic polymeric microbead. In embodiments, the microparticle is a carboxymethyldextran functionalized microbead. In embodiments, the microparticle is a polytheylene glycol functionalized microbead. In further embodiments, the polytheylene glycol functionalized microbead includes orthogonally protected amines. In embodiments, the microparticle is a magnetic microbead. In embodiments, the microparticle is a metallic microbead. In embodiments, the microparticle is a silica microbead.

As depicted in FIG. 1 the microparticles provided herein including embodiments thereof may include a plurality of attachment points for the attachment of a plurality of a first, second and third linker. The microparticle may include a plurality of first attachment points for the first linker attaching the ligand domain, a plurality of second attachment points for the second linker attaching the nucleic acid domain and a plurality of third attachment points for the third linker attaching the microparticle to a solid support. The total number of attachment points per microparticle may be about 25-50 attomoles. Where the total number of attachment points corresponds to 100%, the number of first attachment points may be more than about 1% and less than about 20%. Where the total number of attachment points corresponds to 100%, the number of second attachment points may be more than about 40% and less than about 90%. Where the total number of attachment points corresponds to 100%, the number of third attachment points may be more than about 0% and less than about 50%.

A "ligand domain" as provided herein is a domain capable of binding a ligand binder (e.g., analyte, biomolecule). In embodiments, the ligand domain is a peptide. In embodiments, the ligand domain is a polypeptide. In embodiments, the ligand domain includes a surface glycoprotein or fragments thereof. In embodiments, the ligand domain has a protein sequence corresponding to amino acid position 98-106 of Human influenza hemagglutinin (HA) protein. In embodiments, the ligand domain includes the sequence of SEQ ID NO:17 or SEQ ID NO:18.

In embodiments, the ligand domain includes a protecting moiety attached to a reactive moiety (e.g., a carboxyl functional group) of the ligand domain. As used herein, a protecting moiety is a chemical moiety covalently attached to a ligand domain that prevents the ligand domain from binding a ligand binder, wherein the protecting moiety may be removed, for example, by chemical means when desired. In embodiments, the protecting moiety is fluorenylmethyloxycarbonyl. In embodiments, the protecting moiety is tert-butyl or carboxybenzyl. Where the ligand domain includes a protecting moiety the ligand domain may be a side chain protected polyamide. Where the ligand domain includes a protecting moiety it may also be referred to herein as "synthetic intermediate" or "synthetic precursor." In embodiments, the protecting moiety includes an amino acid side chain. In embodiments, the protecting moiety includes an amino terminus (e.g. a terminal —$NH_2$ group) or a carboxy terminus (e.g. a terminal —COOH group). In embodiments, the protecting moiety is attached to an amino acid side chain. In embodiments, the protecting moiety is attached to an amino terminus (e.g. a terminal —$NH_2$ group) or a carboxy terminus (e.g. a terminal —COOH group). In the presence of the protecting moiety the ligand domain is not capable of binding a ligand binder. Thus, in embodiments the ligand domain includes a protecting moiety and is not bound to a ligand binder. Upon removal of the protecting moiety and reacting the reactive moiety with a ligand domain capable of binding a ligand binder is formed.

The ligand domain provided herein may be formed using any multi-step support-bound synthesis compatible with the composition of the microparticle and with the synthesis chemistry of the nucleic acid domain provided herein. The ligand domain and the nucleic acid domain may be simultaneously synthesized on the microparticle. Alternatively, the nucleic acid domain is synthesized on the microparticle after the synthesis of the ligand domain. In embodiments, the attachment of the ligand domain through the first linker is performed prior to the attachment of the nucleic domain through the second linker. In embodiments, the attachment of the ligand domain through the first linker is performed simultaneously with the attachment of the nucleic domain through the second linker. In embodiments, the ligand domain is a peptide. In embodiments, the ligand domain is a small molecule. In embodiments, the ligand domain is a protein. In embodiments, the ligand domain binds to a ligand binder. The ligand domain may be attached to a detectable moiety (e.g., a fluorescent moiety, luminescent moiety, colorimetric moiety, phosphorescent moiety, radioactive moiety or electroactive moiety).

A "ligand binder" as used herein refers to an agent (e.g., atom, molecule, ion, molecular ion, compound or particle) capable of binding a ligand domain provided herein including embodiments thereof. Ligand binders include without limitation, biomolecules (e.g., hormones, cytokines, proteins, nucleic acids, lipids, carbohydrates, cellular membrane antigens and receptors (neural, hormonal, nutrient, and cell surface receptors or their ligands); whole cells or lysates thereof (e.g., prokaryotic (e.g., pathogenic bacteria), eukaryotic cells (e.g., mammalian tumor cells); viruses (e.g., retroviruses, herpesviruses, adenoviruses, lentiviruses); and spores); chemicals (e.g., solvents, polymers, organic materials); therapeutic molecules (e.g., therapeutic drugs, abused drugs, antibiotics); or environmental pollutants (e.g., pesticides, insecticides, toxins). The ligand binder may be a protein, a mixture of proteins, a nucleic acid, a mixture of nucleic acids, a small molecule, a mixture of small molecules, an element, a mixture of elements, a synthetic polymer, a mixture of synthetic polymers, cell lysate. In embodiments, the ligand binder is a biomolecule. In embodiments, the biomolecule is a nucleic acid. In embodiments, the biomolecule is a protein (e.g. antibody). In embodiments, the ligand binder is an antibody. In embodiments, the ligand binder is an anti-HA antibody. In embodiments, the ligand binder is an anti-Myc antibody. In embodiments, the ligand domain binds a peptide of SEQ ID NO:17. In embodiments, the ligand domain binds a peptide of SEQ ID NO:18. In embodiments, the ligand binder is attached to a detectable moiety. In embodiments, the detectable moiety is a fluorescent moiety. In embodiments, the ligand binder is a small molecule. In embodiments, the ligand domain is not bound to a ligand binder. Where the ligand domain is not bound to a ligand binder, the ligand domain may include a protecting moiety or any other applicable modification rendering the ligand domain inert. The ligand binder may be attached to a detectable moiety (e.g., a fluorescent moiety, luminescent moiety, colorimetric moiety, phosphorescent moiety, radioactive moiety or electroactive moiety).

As described above a "nucleic acid domain" as provided herein includes a nucleic acid sequence corresponding to the individual building blocks of the ligand domain and the order in which these building blocks are incorporated in said ligand domain. Therefore, each microparticle includes a unique ligand domain and a corresponding nucleic acid domain encoding specific nucleic acid sequences corresponding to the building blocks of the ligand domain and the order in which they were incorporated in the ligand domain. The nucleic acid domains provided herein are also referred to as "tag" or "encoding tag." In embodiments, the nucleic acid domain includes a nucleic acid sequence. In embodiments, the nucleic acid sequence is about 18 base pairs in length. In embodiments, the nucleic acid sequence is about 20 base pairs in length. In embodiments, the nucleic acid sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 79, 71, 72, 73, 74, 75, 76, 77, 78, 79, or 80 base pairs in length. In embodiments, the nucleic acid sequence does not include cytosine.

In embodiments, the nucleic acid sequence includes a covalent linker. In embodiments, the covalent linker connects two nucleic acid sequences within a nucleic acid domain. In embodiments, the nucleic acid domain includes at least two nucleic acid sequences connected through a covalent linker. In embodiments, the nucleic acid domain includes at least four nucleic acid sequences connected through covalent linkers. Thus, in embodiments, the nucleic acid domain includes a first nucleic acid sequence, a second nucleic acid sequence, a third nucleic acid sequence and a forth nucleic acid sequence, wherein the first nucleic acid sequence is connected to the second nucleic acid sequence through a first covalent linker, the second nucleic acid sequence is connected to the third nucleic acid sequence through a second covalent linker and the third nucleic acid sequence is connected to the forth nucleic acid sequence through a third covalent linker. In embodiments, the covalent linker (e.g., first, second, third covalent linker) is a bond, —S(O)—, —S(O)$_2$NH—, —NHS(O)$_2$—, —C(O)O—, —OC(O)—, —C(O), —C(O)NH, —NH—, —NHC(O)—, —O—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the covalent linker is a 1,3 triazolene linker. In embodiments, the covalent linker has the structure:

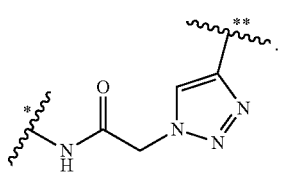

(I)

In embodiments, the covalent linker includes the structure:

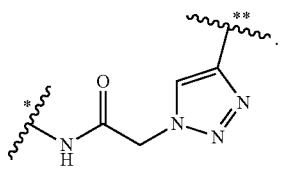

(I)

In formula (I), the point of attachment marked by * indicates the attachment of the covalent linker to a first nucleic acid sequence and the attachment marked by ** indicates attachment point of the covalent linker to a second nucleic acid sequence.

Figure 4:
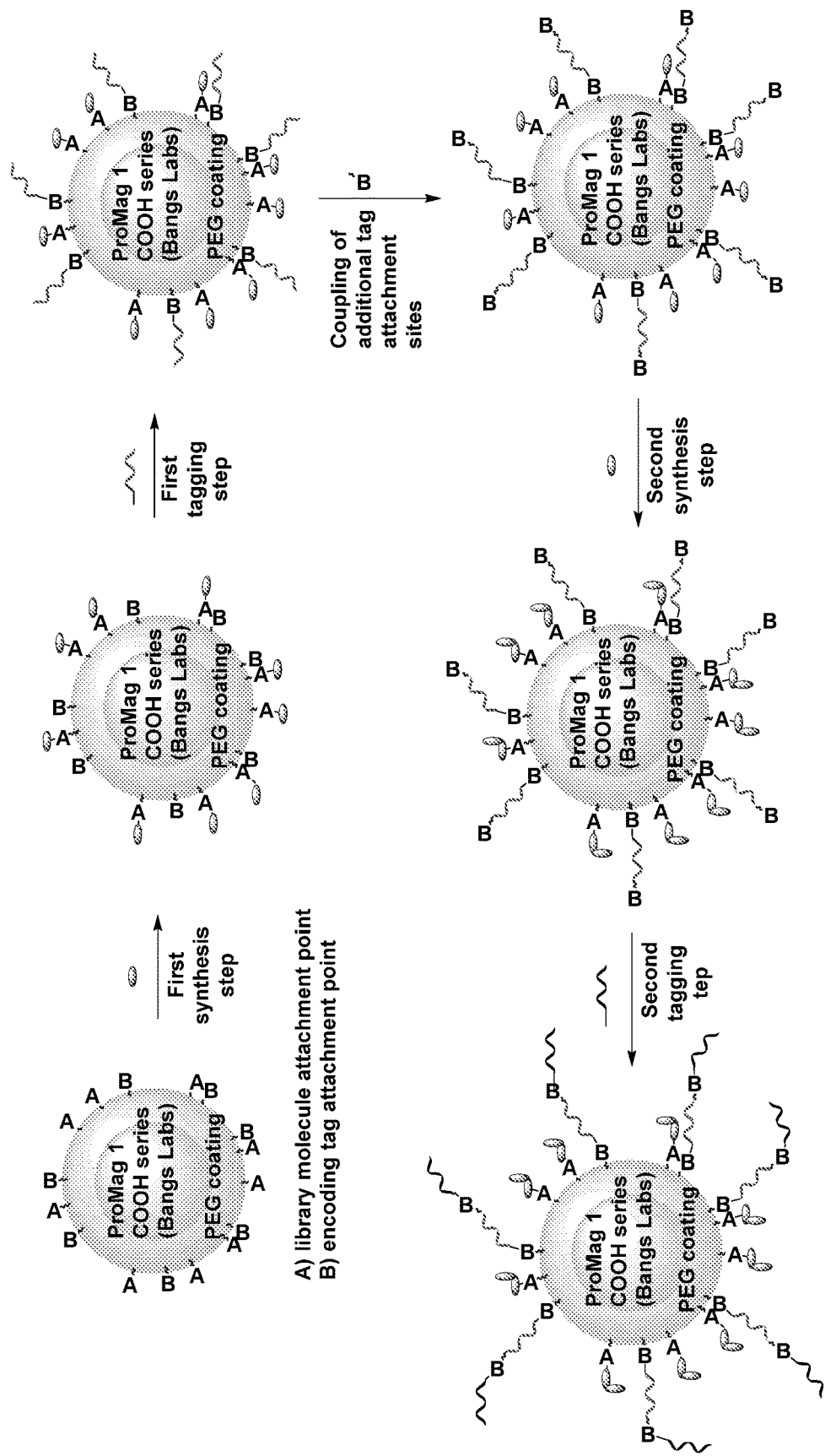
FIG. 4: Schematic illustrating the connectivity of the nucleic acid tags in one of the potential tagging approaches. In this variant, during each tagging step, all of the tag attachment points on the microparticles are consumed, and an equivalent amount of new tag attachment points are then created on the ends of the newly attached nucleic acid tags. Two tagging steps in this example would lead to the generation of predominantly a single population of nucleic acid containing oligomers on each bead consisting of tag 1 linked to tag 2. Note that by design, each tag population is independently decodable, such that decodability is only dependent on the presence of each individual tag—i.e. decodability of tag 2 is not dependent on being directly attached to tag 1 and vice versa—such that subsets of beads which may have not gone to complete conversion in either tagging step are still decodable, as long as sufficient amounts of each tag are present for decoding.
Figure 5:
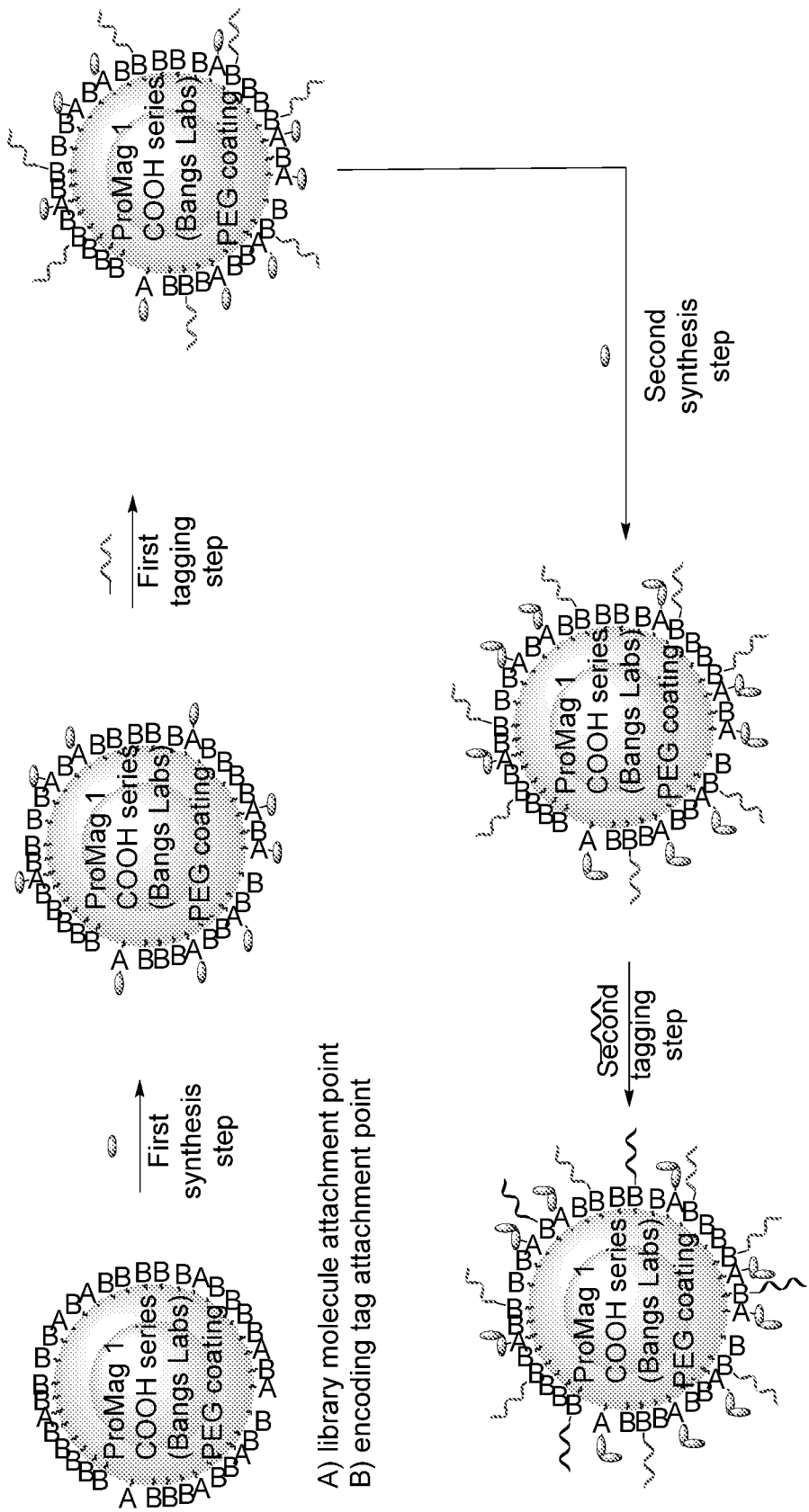
FIG. 5: Schematic illustrating the connectivity of the nucleic acid tags in one of the potential tagging approaches. In this variant, during each tagging step, only a fraction of the tag attachment points on the microparticle for the tags are consumed. As shown, two tagging steps in this example would lead to the generation two populations of nucleic acid containing oligomers on each bead-one population consisting of tag 1 and one population consisting of tag 2. For four tagging steps, four unique populations per bead would be generated.
Figure 6:
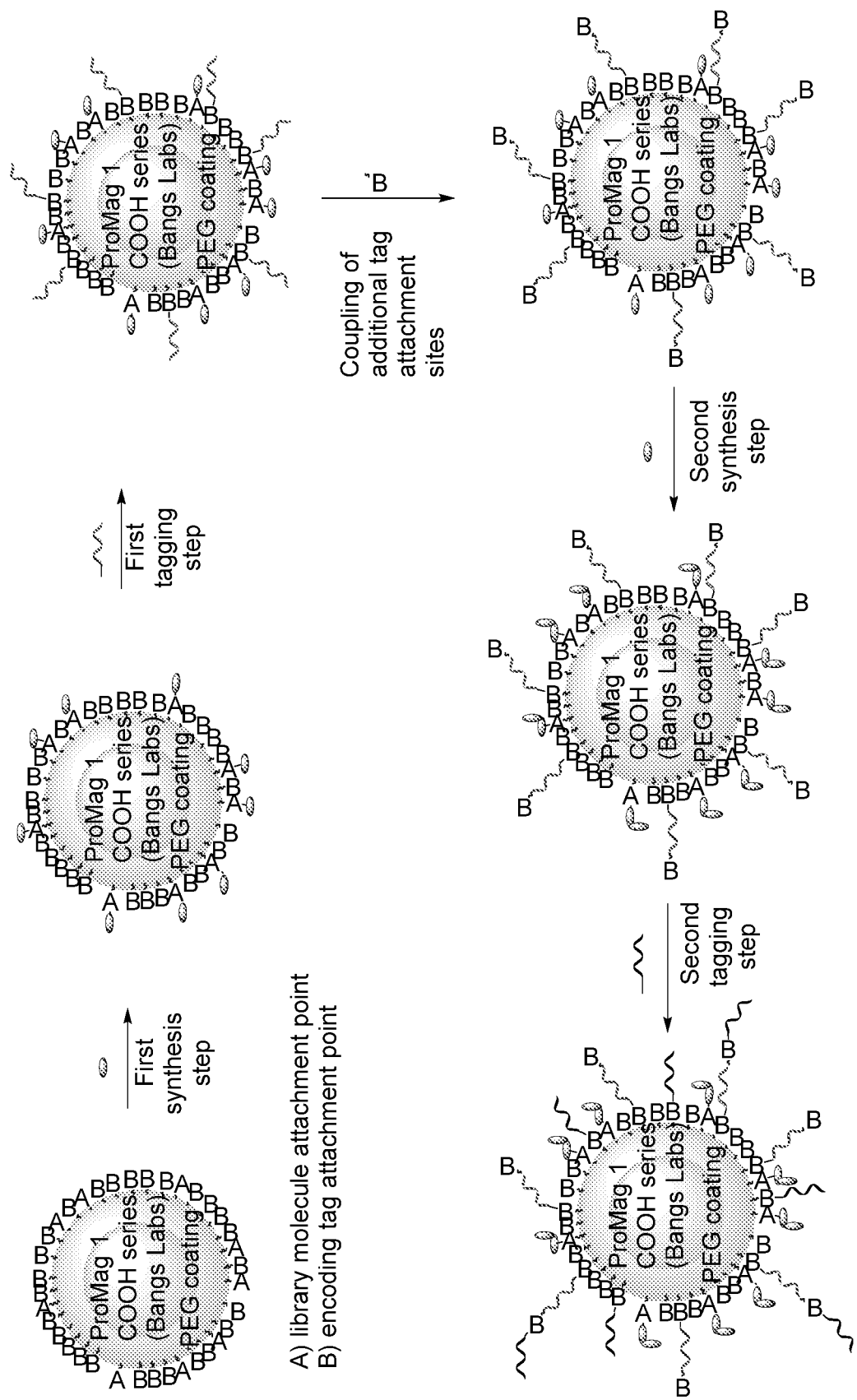
FIG. 6: Schematic illustrating the connectivity of the nucleic acid tags in one of the potential tagging approaches. In this variant, during each tagging step, a fraction of the tag attachment points on the microparticles are consumed, and an equivalent amount of new tag attachment points are then created on the ends of the newly attached nucleic acid tags. Two tagging steps in this example would lead to the generation of three populations of nucleic acid containing oligomers on each bead, tag 1, tag 2, and an oligomer consisting of tag 1 linked to tag 2. Note that by design, each tag population is independently decodable, such that decodability of each tag is only dependent on the presence of each individual tag—ie decodability of tag 2 is not dependent on being directly attached to tag 1 and vice versa.
Figure 7:
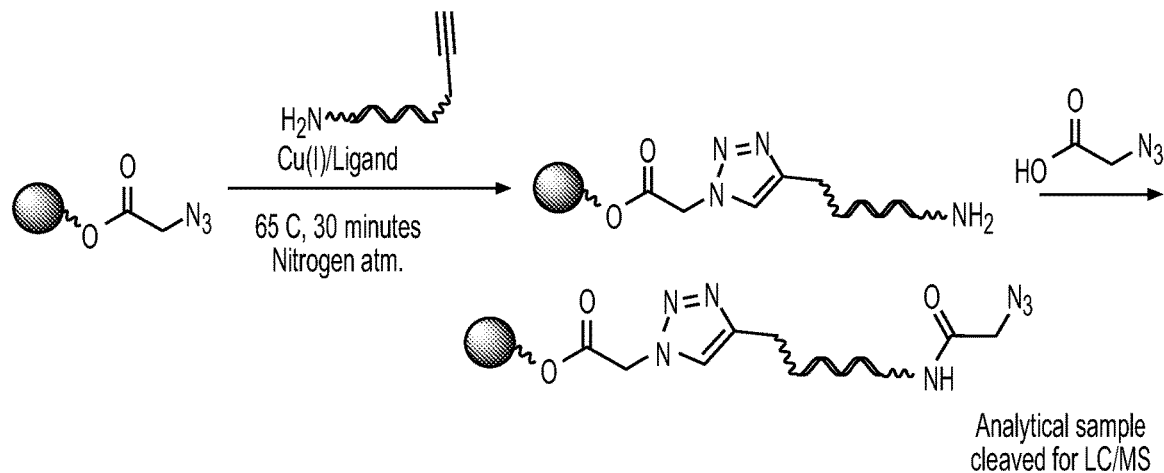
FIG. 7: LC traces of the different tag intermediates during one round of tagging and the addition of a new tag linking element. As demonstrated by changes in retention time and mass spectra, the solid phase cycloaddition chemistry yields predominantly the desired product. Following the solid phase amide coupling of a new tag linking element, LC/MS analysis indicates conversion to the desired product. See materials and methods for cycloaddition conditions, amide coupling conditions, and cleavage conditions.
Figure 7:
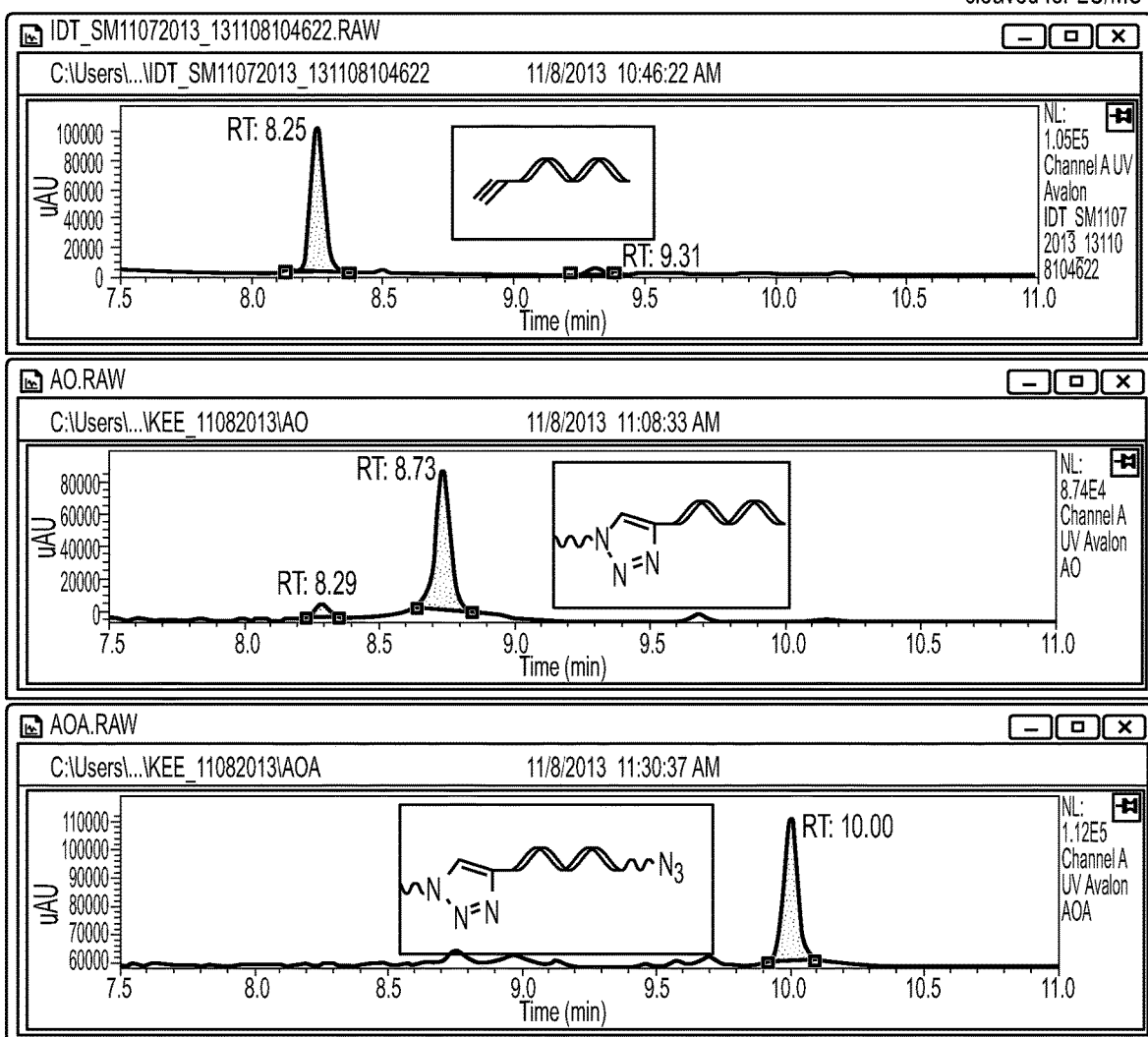
Figure 8:
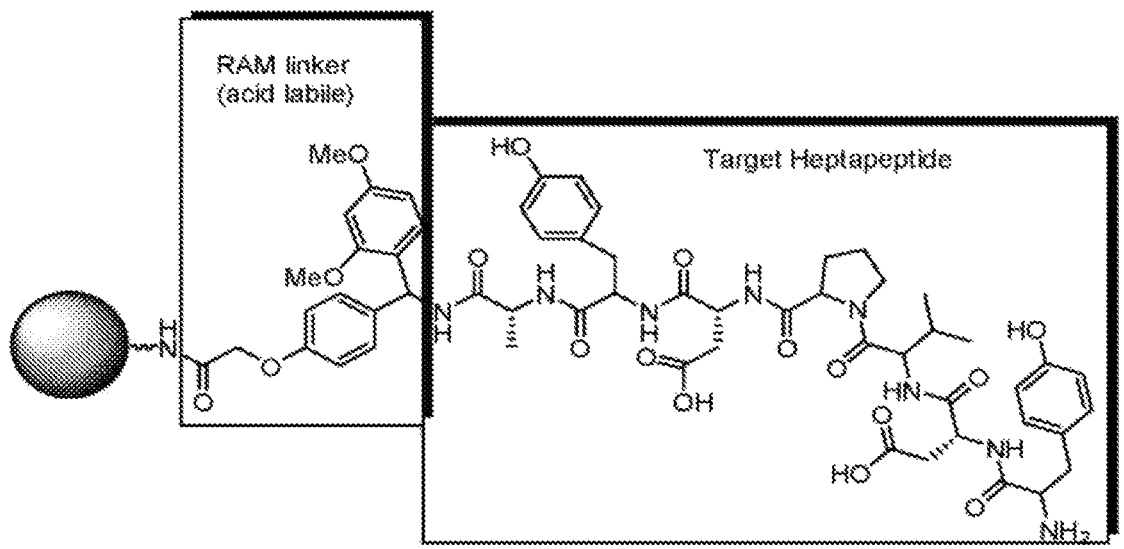
FIG. 8: A portion of the PEG modified microparticles was functionalized with an acid labile linker and submitted to a seven step solid phase peptide synthesis. The product was cleaved from the microparticles using TFA. The TFA was removed and residue was analyzed by mass spectrometry, demonstrating successful synthesis of the desired peptide.
Figure 8:
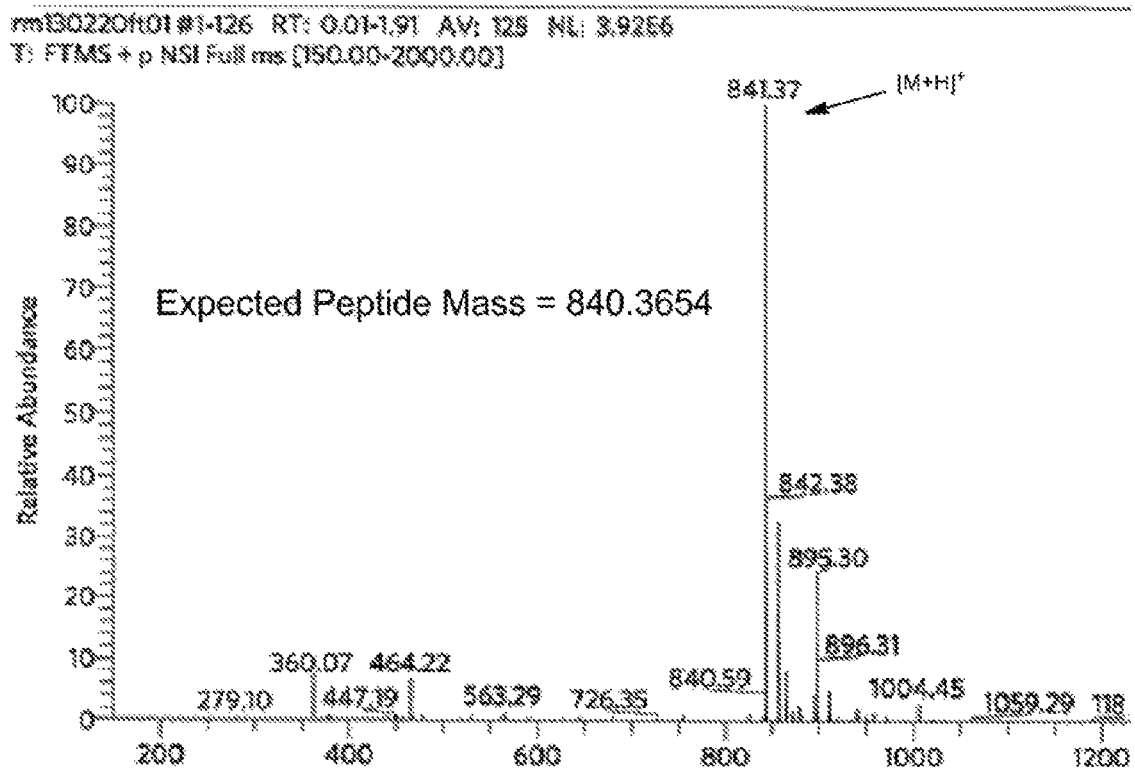
Figure 9A:
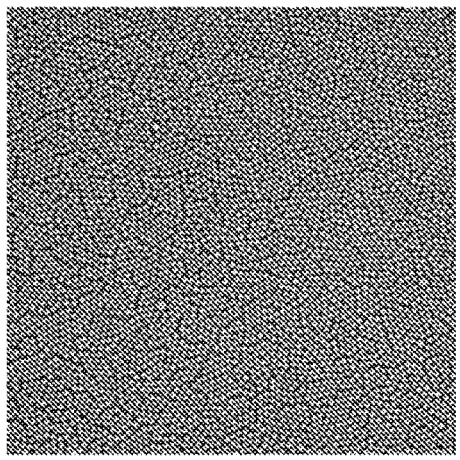
FIG. 9A-9B: Demonstration of two different modes of library immobilization.
Figure 9B:
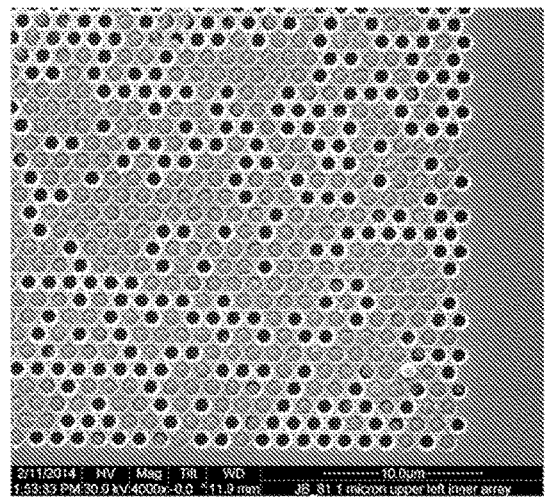
Figure 10:
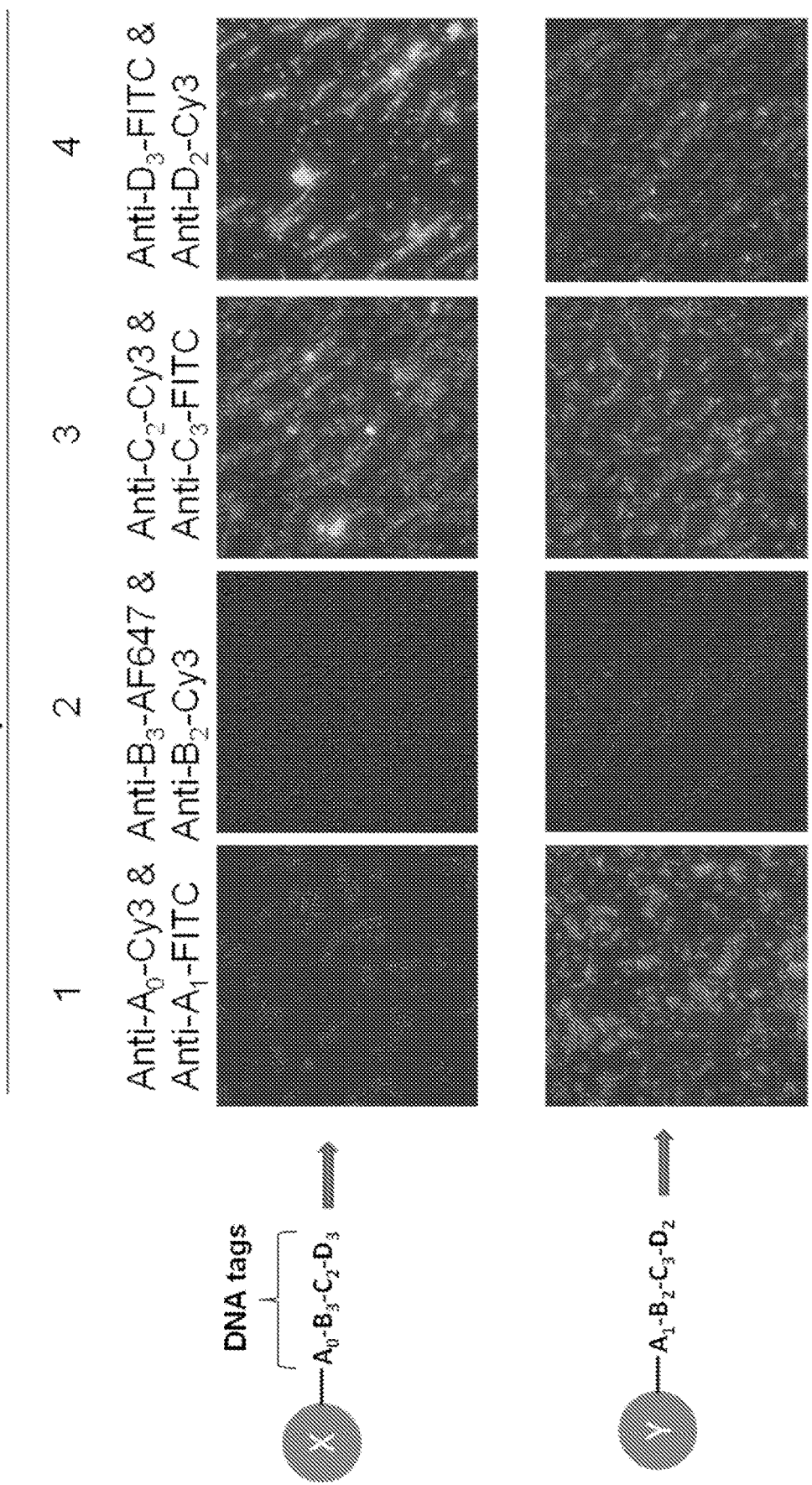
FIG. 10: Microparticles undergoing four rounds of encoding/tagging steps (as outlined in Encoding Scheme of FIG. 6 can be successfully decoded. Two different portions of microparticles were submitted in parallel to four rounds of tagging as illustrated in FIG. 6. Each portion of microparticles was tagged with a unique 18mer at each tagging step. Following the four rounds of encoding, each portion was exposed to a series of hybridization solutions containing a 1:1 mixture of two different fluorescently labeled oligonucleotide probes. Shown are eight different two-channel fluorescent images of aliquots of the tagged microparticles following hybridization. In column 1, the two microparticle samples were hybridized with a 1:1 mixture of Cy3 labeled oligonucleotide complementary to A0, and a FITC labeled oligonucleotide complementary to A1. As expected, those particles encoded with tag A0 fluoresced in the red (Cy3) channel (top image, column 1) and those particles encoded with tag A1 fluoresced in the green (FITC) channel (bottom image, column 2). The trend holds true for all of the other hybridization conditions, in which particles selectively fluoresce in the wavelength corresponding to the fluorescent label attached to the complementary DNA sequence tag, rather than a mismatched tag.
Figure 11:
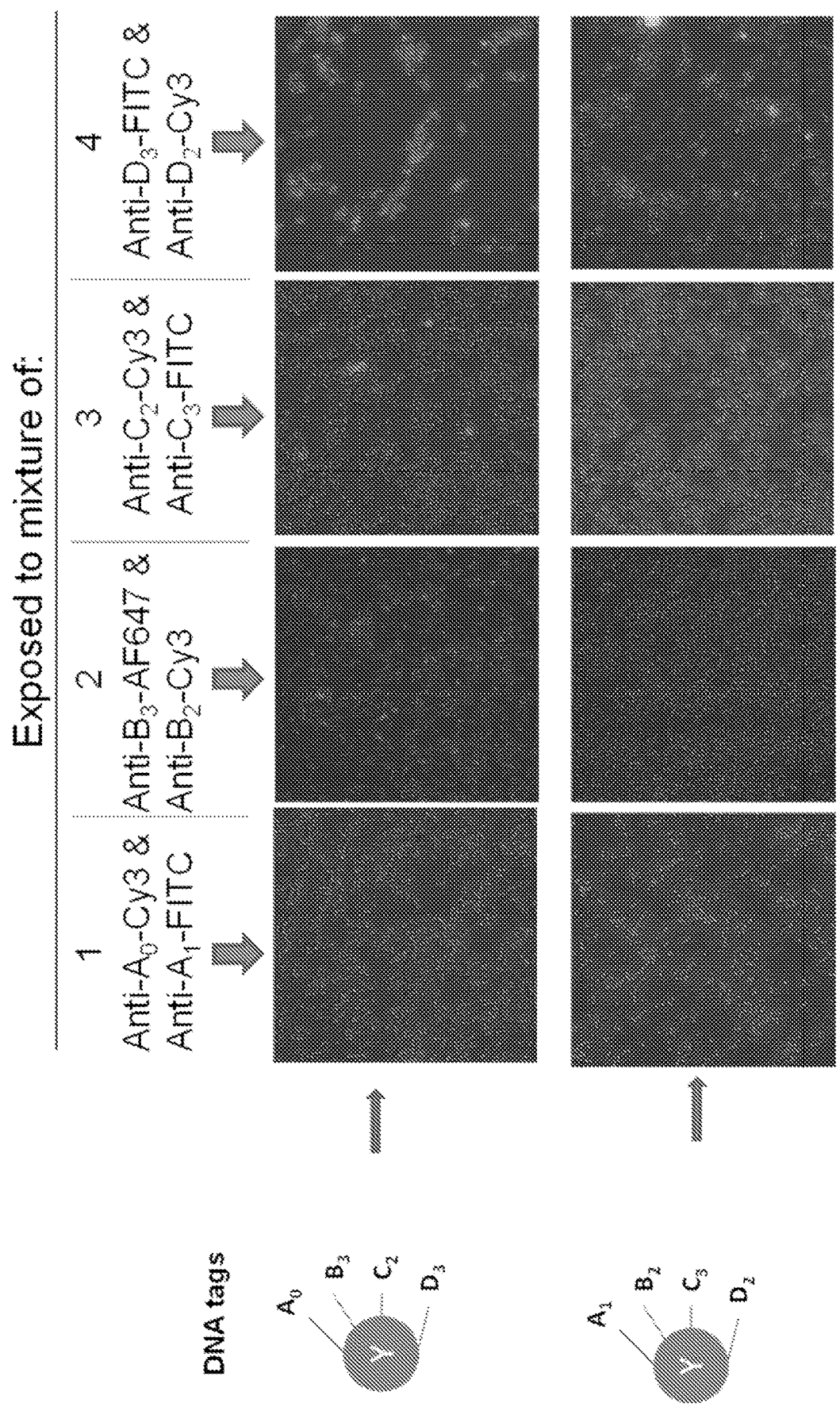
FIG. 11: Microparticles undergoing four rounds of encoding/tagging steps (as outlined in FIG. 5 can be successfully decoded. Two different portions of microparticles were submitted in parallel to four rounds of tagging as illustrated in FIG. 5. Each portion of microparticles was tagged with a unique 18mer at each tagging step. Following the four rounds of encoding, each portion was exposed to a series of hybridization solutions containing a 1:1 mixture of two different fluorescently labeled oligonucleotide probes. Shown are eight different two-channel fluorescent images of aliquots of the tagged microparticles following hybridization. In column 1, the two microparticle samples were hybridized with a 1:1 mixture of Cy3 labeled oligonucleotide complementary to A0, and a FITC labeled oligonucleotide complementary to A1. As expected, those particles encoded with tag A0 fluoresced in the red (Cy3) channel (top image, column 1) and those particles encoded with tag A1 fluoresced in the green (FITC) channel (bottom image, column 2). The trend holds true for all of the other hybridization conditions, in which particles selectively fluoresce in the wavelength corresponding to the fluorescent label attached to the complementary DNA sequence tag, rather than a mismatched tag.
Figure 12:
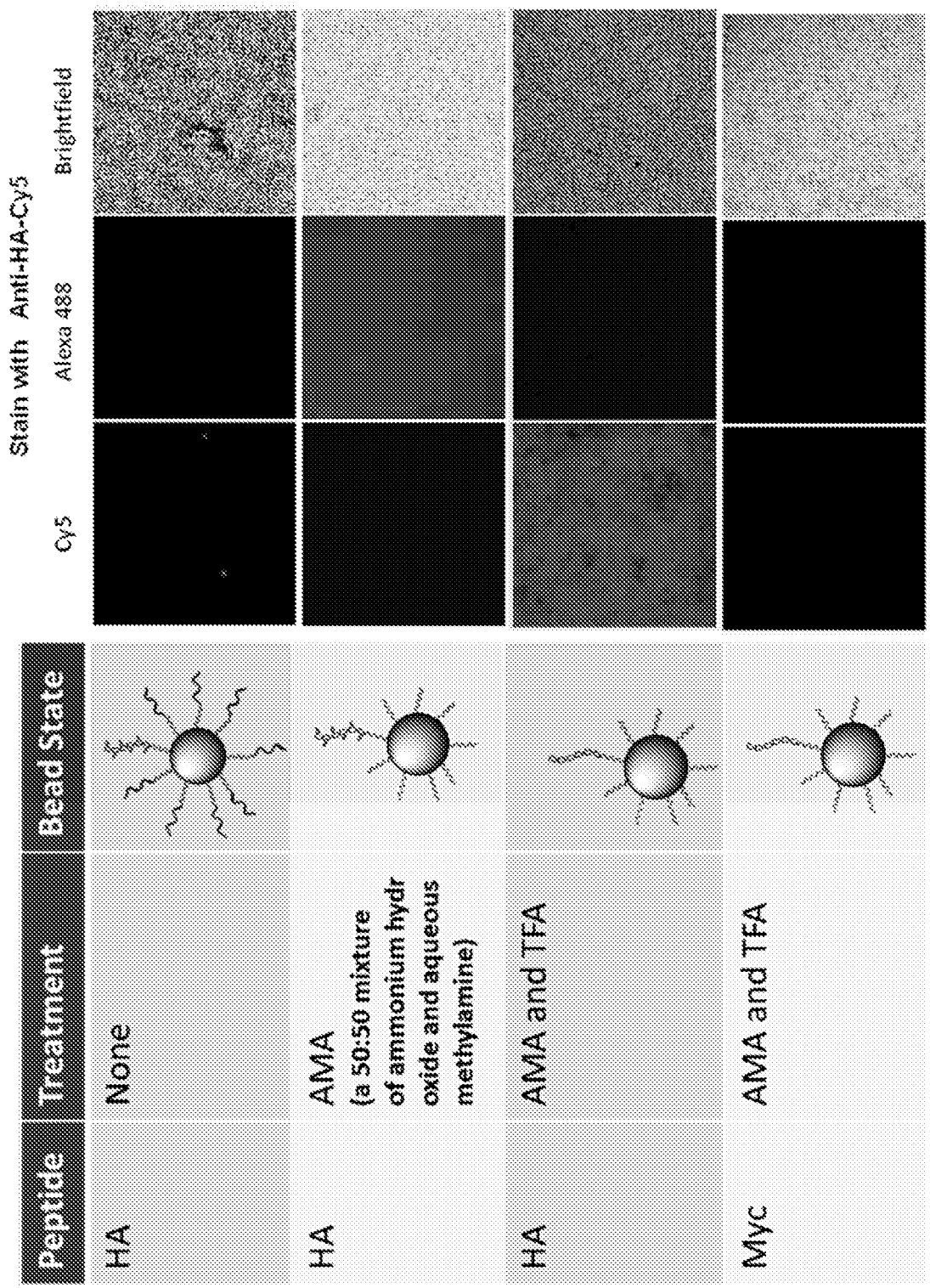
FIG. 12: To demonstrate peptide synthesis is compatible with Applicants' encoding chemistry, two peptides (HA and Myc—two common antibody epitopes) were synthesized in parallel on the microparticles in which four of the synthetic steps were encoded with DNA tags. The particles were incubated with a Cy5 labeled antibody specific to the HA epitope at various steps in the synthesis. Microparticles that displayed DNA tags and fully protected HA peptide (in which the side chain protecting moieties have not been removed) did not bind the labeled antibody (top row images). Following cleavage of the DNA tags, the microparticles that display side chain protected HA peptide do not bind the labeled antibody (second row images). Following deprotection of the side chain protecting moietiess (TFA treatment), the HA displaying microparticles now bind the labeled antibody (third row images). Microparticles displaying fully deprotected Myc peptide does not bind the labeled antibody (fourth row images)
Figure 13:
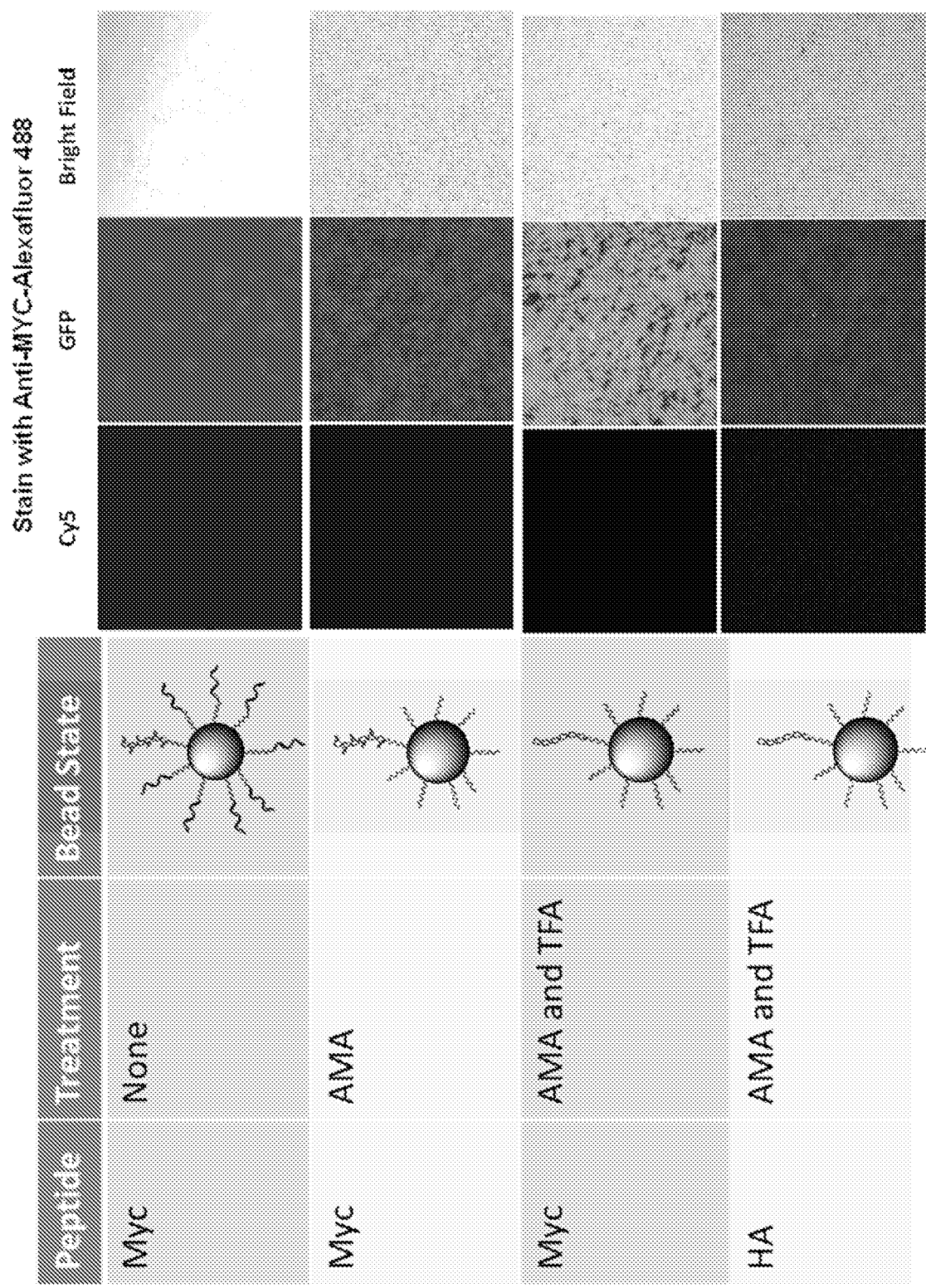
FIG. 13: To demonstrate peptide synthesis is compatible with Applicants' encoding chemistry, two peptides (HA and Myc—two common antibody epitopes) were synthesized in parallel on microparticles in which four of the synthetic steps were encoded with DNA tags. The particles were incubated with an Alexafluor 488 labeled antibody specific to the Myc epitope at various steps in the synthesis. Microparticles that displayed DNA tags and fully protected Myc peptide (in which the side chain protecting moietiess have not been removed) did not bind the labeled antibody (top row images). Following cleavage of the DNA tags, the microparticles that display side chain protected Myc peptide do not bind the labeled antibody (second row images). Following deprotection of the side chain protecting moietiess (TFA treatment), the Myc displaying microparticles now bind the labeled antibody (third row images). Microparticles displaying fully deprotected HA peptide does not bind the labeled antibody (fourth row images)
Figure 14:
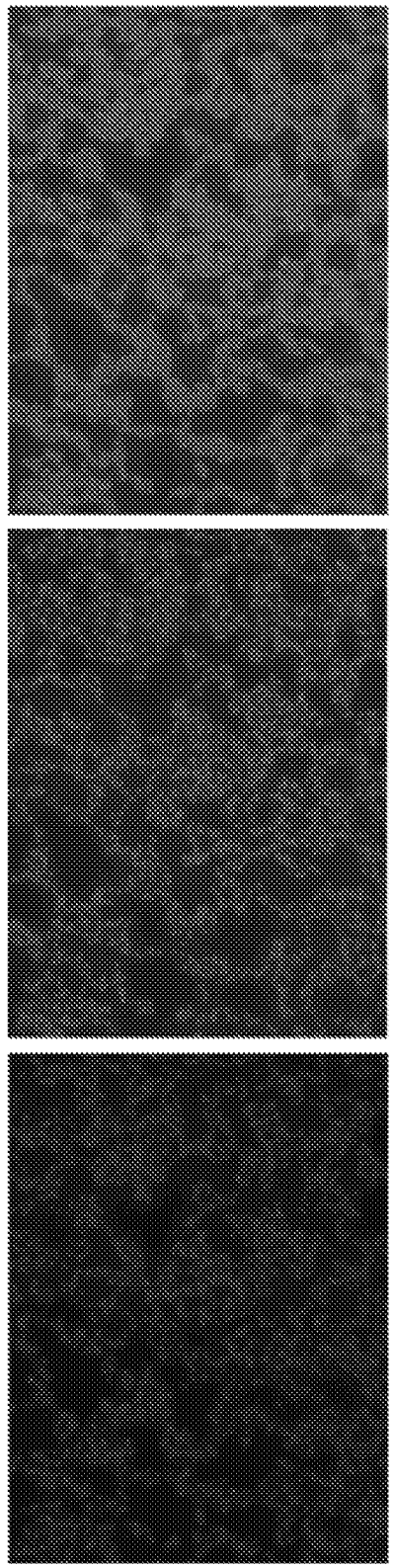
FIG. 14: Mixing the beads and stains demonstrates ability to differentiate binding. Tagless beads bearing fully deprotected HA peptide or Myc peptide were mixed and stained with a mixture of Anti-HA-Cy5 and Anti-Myc-Alexa 488. Fluorescence imaging indicates two distinct bead populations.
Figure 15B:
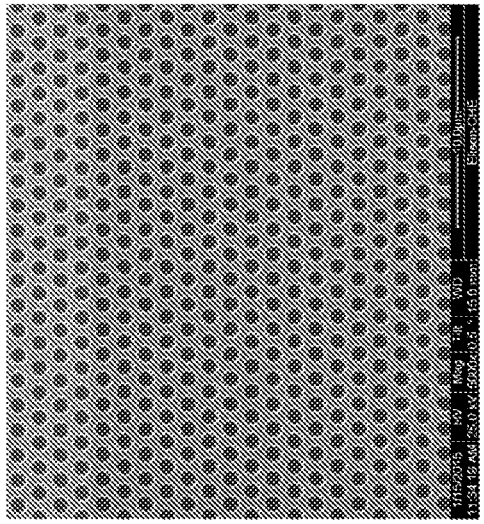
FIG. 15A-FIG. 15H.
Figure 15D:
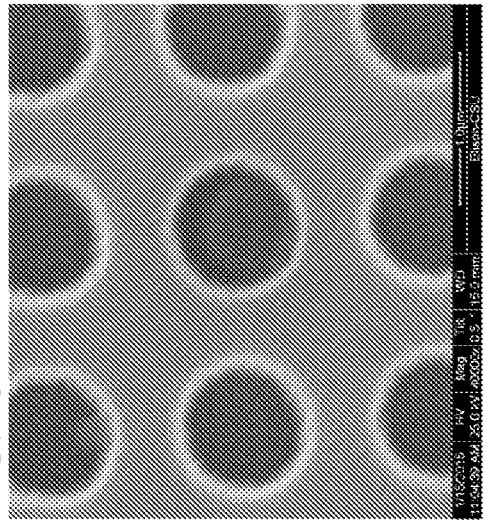
Figure 15A:
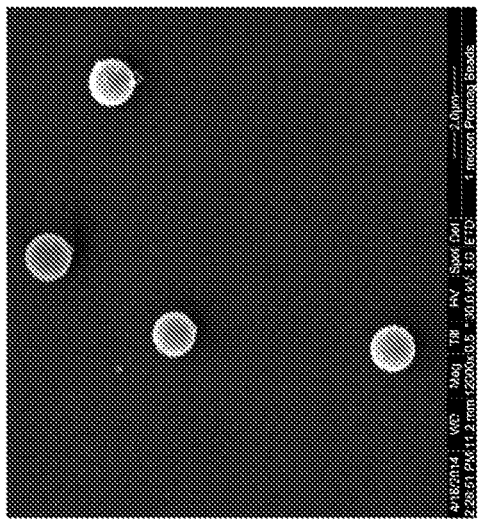
Figure 15C:
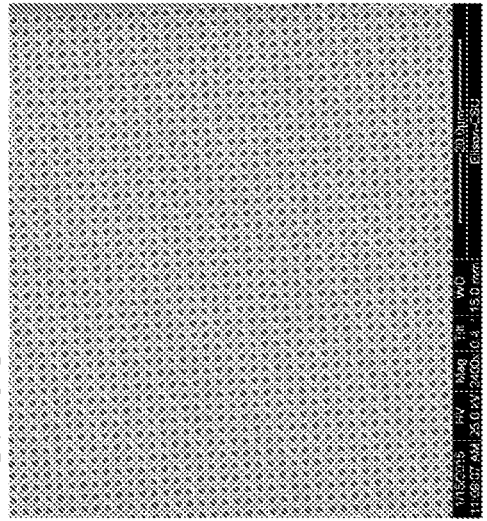
Figure 15F:
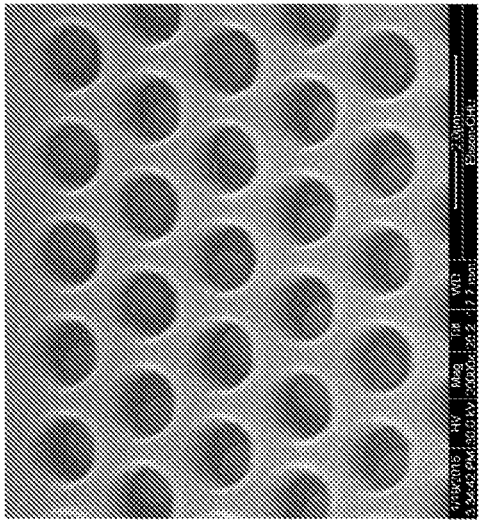
Figure 15H:
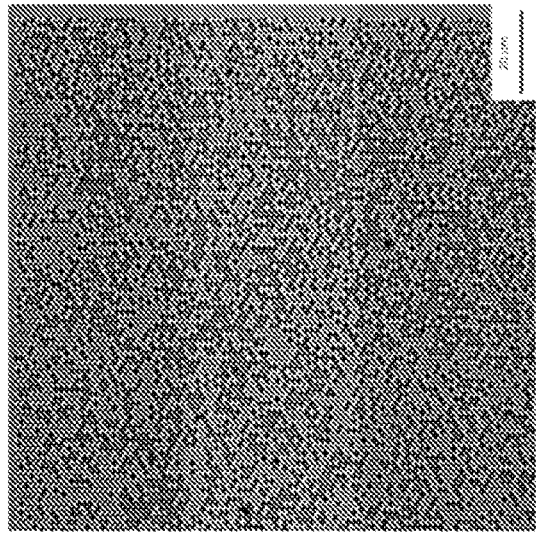
Figure 15E:
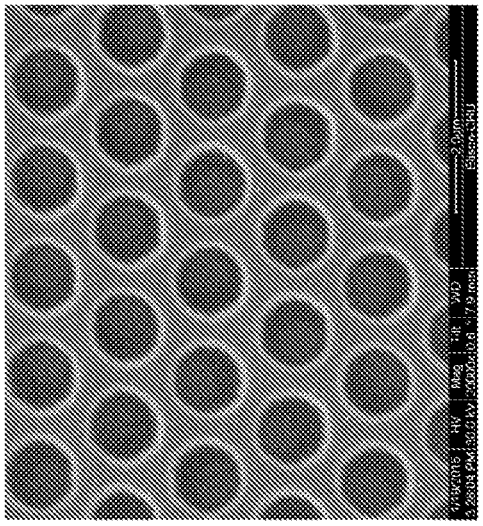
Figure 15G:
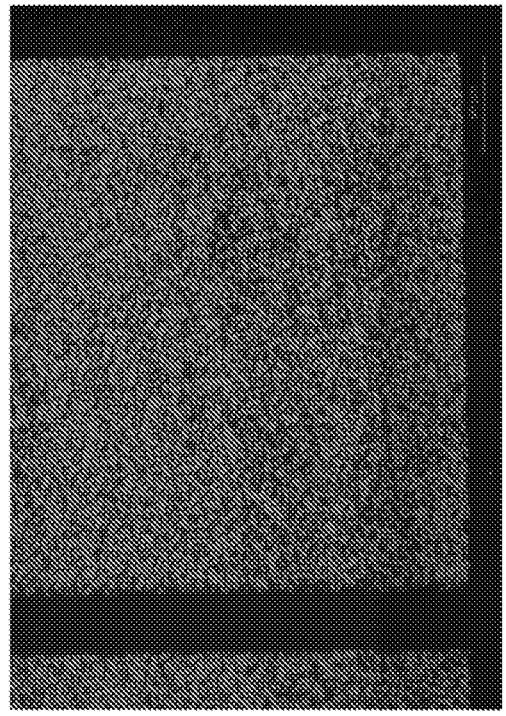

In embodiments, the nucleic acid domain includes a functionalized nucleic acid sequence. A functionalize nucleic acid as provided herein includes reactive functional groups used for conjugate chemistries as described herein. In embodiments, the nucleic acid domain includes a plurality of functionalized nucleic acid sequences. Where the nucleic acid domain includes a plurality of functionalized nucleic acid sequences, the functionalized nucleic acid sequences are connected through a plurality of covalent linkers. In embodiments, each of the plurality of covalent linkers is chemically different. Schematic illustrations of the synthesis of the nucleic domain and ligand domain on a microparticle are depicted in FIGS. 4, 5, and 6. As depicted in FIGS. 5 and 6 the nucleic acid domains attached to a microparticle may be independently different depending on the synthesis used and may include two or more nucleic acid sequences connected through a covalent linker.

The nucleic acid domains provided herein including embodiments thereof are compatible with (i) the multi-step support-bound synthesis methods applied to form a ligand domain as provided herein, (ii) the composition of the microparticle and (iii) the decoding procedures provided herein (i.e., identifying the composition of the ligand domain and its location on an array). Useful decoding procedures include without limitation sequencing by hybridization or enzymatic-based sequencing procedures (e.g., sequencing by synthesis, sequencing by ligation). Thus, in embodiments, the nucleic acid sequence is bound to a complementary nucleic acid sequence. In embodiments, the complementary nucleic acid sequence includes a detectable moiety. In embodiments, the detectable moiety is a fluorescent moiety. Upon hybridization of a complementary nucleic acid to said nucleic acid domain, the composition of the ligand domain and its location on the array can be determined. After the identity of the ligand domain and its location on the array have been determined the nucleic acid domain may be removed (e.g., through cleavage of the second linker), the ligand domain may be further modified (e.g., through reacting a reactive moiety of the ligand domain) and contacted with a ligand binder (e.g., biomolecule).

The linkers provided herein chemically link the microparticle and the ligand domain (first linker), the microparticle and the nucleic acid domain (second linker) or the microparticle and the solid support (third linker). As described above the nucleic acid domain provided herein including embodiments thereof may include two or more nucleic acid sequences connected through covalent linkers (e.g., a 1,3 triazolene linker). Thus, in embodiments, the nucleic acid domain includes two or more 1,3 triazolene linkers. The linkers provided herein (e.g., first linker, second linker, third linker) may be covalently attached to the microparticle applying methods well known in the art and compatible with the composition of the linker and the microparticle. The linkers provided herein may include the conjugated product of reactive moieties at the point of attachment to the microparticle, at the point of attachment to the ligand domain, at the point of attachment to the nucleic acid domain, or at the point of attachment to the solid support. Thus, the linkers provided herein may be polyvalent and may be formed by conjugate chemistry techniques. Non-limiting examples of linkers useful for the compositions and methods provided herein (e.g., first linker, second linker, third linker) include alkyl groups (including substituted alkyl groups and alkyl groups containing heteroatom moieties), with short alkyl groups, esters, amide, amine, epoxy groups and ethylene glycol or derivatives thereof. The linkers provided herein (e.g., first linker, second linker, third linker) may include a sulfone group, forming sulfonamide, an ester group or an ether group (e.g., triethyl ether).

In embodiments, the first linker is a bond, —S(O)—, —S(O)₂NH—, —NHS(O)₂—, —C(O)O—, —OC(O)—, —C(O)—, —C(O)NH—, —NH—, —NHC(O)—, —O—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the second linker is a bond, —S(O)—, —S(O)₂NH—, —NHS(O)₂—, —C(O)O—, —OC(O)—, —C(O)—, —C(O)NH—, —NH—, —NHC(O)—, —O—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the third linker is a bond, —S(O)—, —S(O)₂NH—, —NHS(O)₂—, —C(O)O—, —OC(O)—, —C(O)—, —C(O)NH—, —NH—, —NHC(O)—, —O—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the first linker includes the structure —N(H)—C(O)—. In embodiments, the first linker includes the structure —N(H)—C(O)—. Where the first linker has the structure —N(H)—C(O)—, the nitrogen is attached to the functionalized solid support (e.g., functionalize with bis-amino PEG 3000) and the carbon is attached to the ligand domain. As described above, after the identity of the ligand domain and its location on the array have been determined, the nucleic acid domain may be removed through cleavage of the second linker. In embodiments, the second linker is a photocleavable linker. In embodiments, the second linker is an acid labile linker. In embodiments, the second linker includes an ester. In embodiments, the second linker is an alkali labile linker. In embodiments, the second linker has the structure:

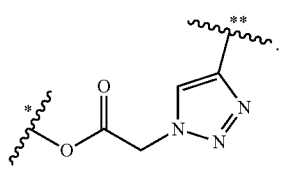

(II)

In embodiments, the second linker includes the structure:

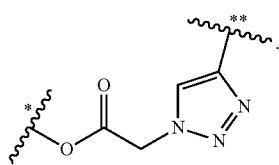

(II)

In formula (II), the point of attachment marked by * indicates the point of attachment to the functionalized solid support (e.g., functionalized with hydroxyl-amine PEG 3000) and the point of attachment marked by ** indicates the point of attachment to the nucleic acid domain. In embodiments, the second linker has the structure:

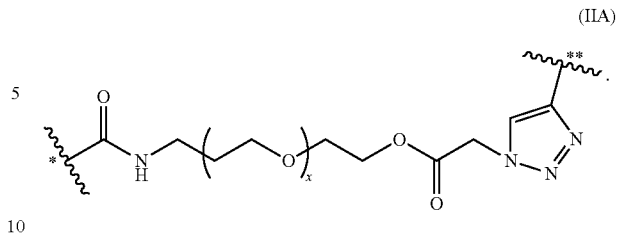

(IIA)

In formula (IIA), X is an integer from 20-300. In embodiments, x is 68. In formula (IIA), the point of attachment marked by * indicates the point of attachment to the solid support and the point of attachment marked by ** indicates the point of attachment to the nucleic acid domain. In embodiments, the second linker has the structure

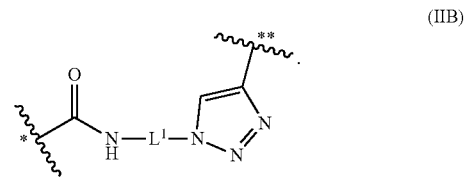

(IIB)

In formula (IIB), $L^1$ is a bond, —S(O)—, —S(O)₂NH—, —NHS(O)₂—, —C(O)O—, —OC(O)—, —C(O)—, —C(O)NH—, —NH—, —NHC(O)—, —O—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In formula (IIB), the point of attachment marked by * indicates the point of attachment to the solid support and the point of attachment marked by ** indicates the point of attachment to the nucleic acid domain.

Figure 3:
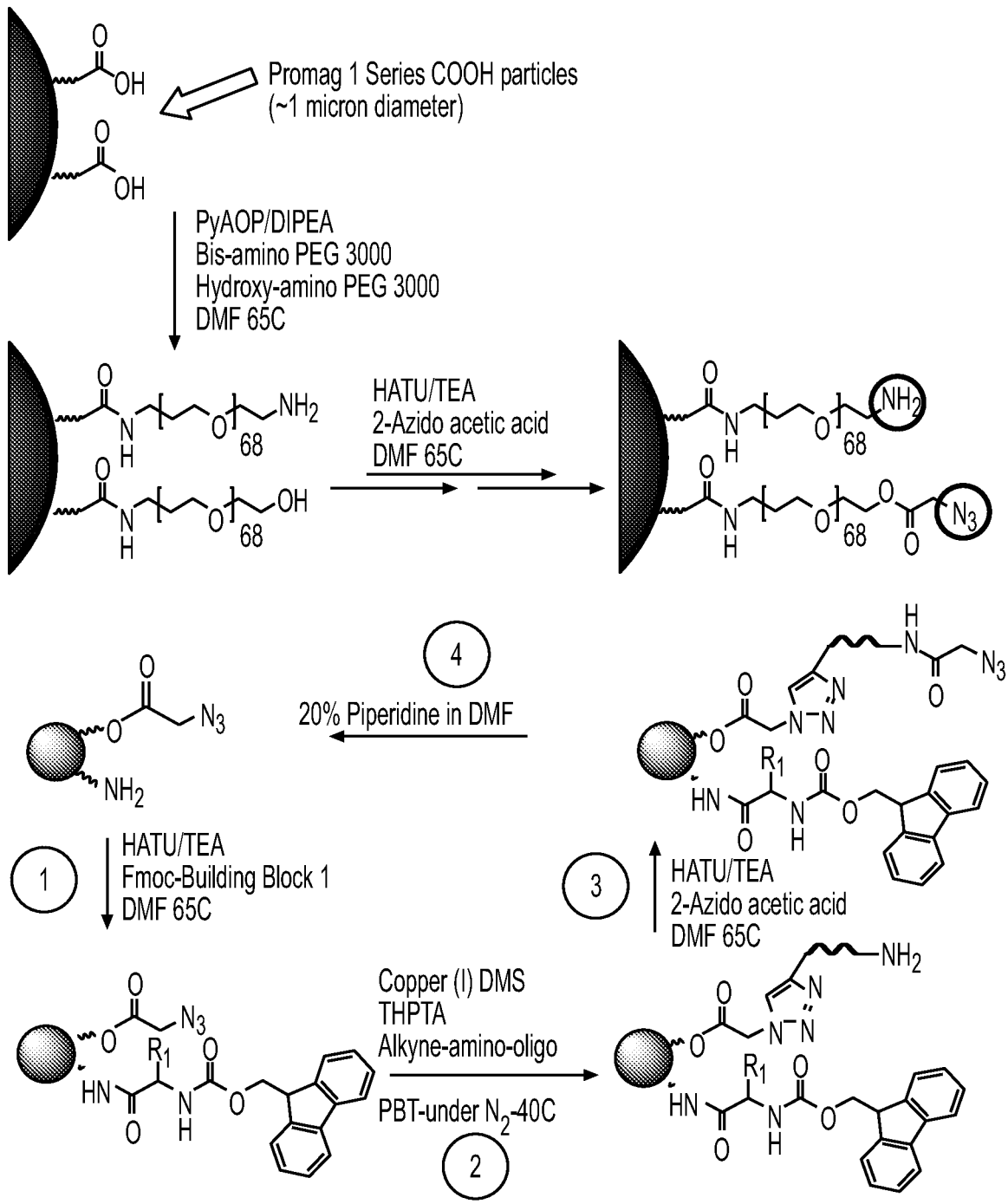
FIG. 3: An illustration of the chemical bonds being formed and broken during one round of an encoded synthesis step using peptide synthesis as the chemistry which is being encoded. In step 1 an Fmoc protected amino acid is coupled to the free amine on the microparticle through an amide coupling. In step 2 a nucleic acid tag bearing an alkyne and free primary amine is coupled to the azide group on the microparticle through a copper catalyzed Huisgen cycloaddition. In step 3, an azide group is coupled to the primary amine on the nucleic acid through an amide coupling. In step 4 the Fmoc group protecting the amine group of the incorporated amino acid is removed. The product following step 4 displays the same reactive moietiess as the starting material (prior to step 1), but contains an additional nucleic acid tag and an additional amino acid. See materials and methods for reaction details. See materials and methods for a detailed example of how initial microparticles are prepared for the orthogonal synthesis.

According to the embodiments provided herein the microparticles provided herein may include a plurality of ligand domains and a plurality of nucleic acid domains attached through a plurality of first linkers and a plurality of second linkers, respectively (see FIG. 3, 4, or 5). Thus, in embodiments, the ligand domain is a plurality of ligand domains attached through a plurality of first linkers. In embodiments, the nucleic acid domain is a plurality of nucleic acid domains attached through a plurality of second linkers. In embodiments, the plurality of nucleic acid domains attached to a single microparticle may be the same or independently different (see FIG. 5 or 6).

The microparticles provided herein including embodiments thereof may be attached to a solid support. In embodiments, the solid support is a planar support. In embodiments, the microparticle is connected through a third linker to the solid support. In embodiments, the microparticle is non-covalently attached to the solid support (e.g. through electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, the microparticle is mechanically attached to the solid support. Where a microparticle is mechanically attached to the solid support it is physically held in place on the support through mechanical means (e.g., a well). In embodiments, a plurality of microparticles are covalently attached to the solid support. In embodiments, the microparticle is attached to the solid support through an amide linker.

Thus, in embodiments, the third linker has the structure —N(H)—C(O)—. In embodiments, the solid support includes carboxymethyldextran. In embodiments, the solid support includes carboxymethyldextran functionalized glass. In embodiments, the solid support is a silicon wafer.

In embodiments, the plurality of microparticles form a disordered array. A "disordered array" as referred to herein is an array of microparticles, wherein the microparticles are randomly assembled on or attached to a solid support and do not form an ordered two- or three-dimensional structure. In embodiments, the plurality of microparticles form an ordered array. In an ordered array, the microparticles are assembled on or attached to a solid support according to an two- or three-dimensional order. For example, a hexagonal array consists of a plurality of microparticles assembled on or attached to a solid support such that each microparticle forms part of a hexagon, wherein each microparticle occupies one angle of the hexagon, and wherein the center of the hexagon is occupied by a seventh microparticle. In embodiments, the plurality of microparticles form an hexagonal array. In embodiments, the plurality of microparticles form a square packed array. A square packed array consists of a plurality of microparticles assembled on or attached to a solid support such that each microparticle forms part of a square or rectangle consisting of at least four microparticles. The formation of arrays is a method well known and used in the art and is described, inter alia, in U.S. Pat. Nos. 6,110,426; 7,615,368; 7,932,213; 6,824,987; 5,143,854; 8,795,967 and Hughes T R et al. (2001) Nat. Biotech. 4, 342-347, which are hereby incorporated in their entirety and for all purposes. In embodiments, at least about $10^6$ of the microparticles are attached to the solid support. In embodiments, each of the microparticles is different. In embodiments, about $10^6$ to $10^9$ of the microparticles are attached to the solid support. In embodiments, about $10^9$ of the microparticles are attached to the solid support. In embodiments, about $10^5$, $10^6$, $10^7$, $10^8$, $10^9$, $10^{10}$ or $10^{11}$ of the microparticles are attached to the solid support. In embodiments, the array includes $10^6$ microparticles per square millimeter.

In embodiments, the array includes at least about 10,000 microparticles per square millimeter. In embodiments, the array includes at least about 20,000 microparticles per square millimeter. In embodiments, the array includes at least about 30,000 microparticles per square millimeter. In embodiments, the array includes at least about 40,000 microparticles per square millimeter. In embodiments, the array includes at least about 50,000 microparticles per square millimeter. In embodiments, the array includes at least about 60,000 microparticles per square millimeter. In embodiments, the array includes at least about 70,000 microparticles per square millimeter. In embodiments, the array includes at least about 80,000 microparticles per square millimeter. In embodiments, the array includes at least about 90,000 microparticles per square millimeter. In embodiments, the array includes at least about 100,000 microparticles per square millimeter. In embodiments, the array includes at least about 200,000 microparticles per square millimeter. In embodiments, the array includes at least about 300,000 microparticles per square millimeter. In embodiments, the array includes at least about 400,000 microparticles per square millimeter. In embodiments, the array includes at least about 500,000 microparticles per square millimeter. In embodiments, the array includes at least about 600,000 microparticles per square millimeter. In embodiments, the array includes at least about 700,000 microparticles per square millimeter. In embodiments, the array includes at least about 800,000 microparticles per square millimeter. In embodiments, the array includes at least about 900,000 microparticles per square millimeter.

In embodiments, the array includes about 200,000 microparticles per square millimeter. In embodiments, the array includes about 789,000 microparticles per square millimeter. In embodiments, the array includes about 591,715 microparticles per square millimeter. In embodiments, the array includes from about 200,000 to about 800,000 microparticles per square millimeter.

In embodiments, the array includes about one microparticle per 4.99 square microns. In embodiments, the array includes about one microparticle per 1.46 square microns. In embodiments, the array includes about one microparticle per 1.69 square microns. In embodiments, the array includes about one microparticle per square micron.

In embodiments, the solid support includes a plurality of wells each of the wells capturing one of the microparticle. In embodiments, the nucleic acid domain is a nucleic acid sequence as described herein. In embodiments, the nucleic acid sequence is bound to a complementary nucleic acid sequence. In embodiments, the complementary nucleic acid sequence includes a detectable moiety. In embodiments, the detectable moiety is a fluorescent moiety.

In another aspect, a solid support attached to a microparticle is provided, wherein the microparticle is covalently attached to (i) a ligand domain through a first linker; and (ii) a cleaved linker moiety. A "cleaved linker moiety" as provided herein is a monovalent chemical moiety formed through the cleavage of a second linker as provided herein including embodiments thereof. In embodiments, the cleaved linker moiety is a remnant of a cleavable linker. In embodiments, the cleaved linker moiety is a primary alcohol. In embodiments, the cleaved linker moiety is an amide. In embodiments, the ligand domain includes a protecting moiety attached to a reacting group. In embodiments, the ligand domain is bound to a ligand binder. In embodiments, the ligand domain is a plurality of ligand domains attached through a plurality of first linkers. In embodiments, the cleaved linker moiety is a plurality of cleaved linker moieties. In embodiments, the solid support is a planar support. In embodiments, the microparticle is non-covalently attached to the solid support. In embodiments, the microparticle is connected through a third linker to the solid support. In embodiments, the microparticle is mechanically attached to the solid support. In embodiments, a plurality of microparticles are attached to the solid support. In embodiments, the plurality of microparticles forms a disordered array. In embodiments, the plurality of microparticles forms an ordered array. In embodiments, the plurality of microparticles forms a hexagonal array. In embodiments, the plurality of microparticles forms a square packed array. In embodiments, at least about 200,000 of the microparticles are attached per square millimeter of solid support and wherein each of the microparticles is different. In embodiments, at least about $10^6$ of the microparticles are attached to the solid support and wherein each of the microparticles is different. In embodiments, the microparticles are attached to the solid support. In embodiments, about $10^9$ of the microparticles are attached to the solid support. In embodiments, the solid support is within a detection device. In embodiments, the detection device detects the ligand binder bound to the ligand domain and identifies a location of the bound ligand binder on the solid support.

Methods

In another aspect, a method of forming a cleaved microparticle is provided. The method includes (i) attaching a microparticle as provided herein including embodiments thereof to a solid support, thereby forming an immobilized microparticle. (ii) The second linker of the immobilized microparticle is cleaved, thereby forming a cleaved microparticle. In embodiments, the method includes prior to the cleaving of step (ii) and after the attaching of step (i), binding a complementary nucleic acid sequence to the nucleic acid domain. In embodiments, the cleaving includes contacting the immobilized microparticle with a cleaving agent. In embodiments, the cleaving agent is an acid. In embodiments, the cleaving agent is trifluoroacetic acid. In embodiments, the cleaving agent is an alkali agent. In embodiments, the cleaving agent is ammonium hydroxide. In embodiments, the cleaving agent is ammonia. In embodiments, the cleaving agent is methylamine. In embodiments, the cleaving agent is a mixture of ammonium hydroxide and methylamine. In embodiments, the cleaving is performed at room temperature. In embodiments, the cleaving agent is UV irradiation. In embodiments, the cleaving agent is light irradiation. In embodiments, the cleaving does not include cleaving the first linker.

In embodiments, the method includes after the cleaving of step (ii), a step (iii) of reacting a reactive moiety of the ligand domain, thereby forming a reactive ligand domain and (iv) binding a ligand binder to the reactive ligand domain. In embodiments, the method includes after the cleaving of step (ii), a step (iii) of binding a ligand binder to the ligand domain. In embodiments, the step (ii) of cleaving includes binding a ligand binder to the ligand domain. Thus, the cleaving of the second linker may occur simultaneously with the binding of a ligand binder to the ligand domain. Alternatively, the binding of a ligand binder to the ligand domain may occur after the cleaving of the second linker. In embodiments, the binding of a ligand binder to the ligand domain includes reacting a reactive moiety of the ligand domain.

In another aspect, a method of detecting a ligand binder is provided. The method includes (i) attaching a microparticle as provided herein including embodiments thereof to a solid support, thereby forming an immobilized microparticle. (ii) A complementary nucleic acid is bound to the nucleic acid domain of the immobilized microparticle and a location of the nucleic acid domain on the solid support is determined, thereby forming a decoded and mapped microparticle. (iii) The second linker of the decoded and mapped microparticle is cleaved, thereby forming a mapped and cleaved microparticle. (iv) A ligand binder is bound to the ligand domain of the mapped and cleaved microparticle; and (v) a location of the bound ligand binder on the solid support is identified, thereby detecting the ligand binder. In embodiments, the cleaving of step (iii) and the binding of step (iv) occur simultaneously. In embodiments, the binding of a ligand binder to the ligand domain includes reacting a reactive moiety of the ligand domain.

In another aspect, a method of detecting a ligand binder is provided. The method includes (i) contacting a ligand binder with a microparticle as provided herein including embodiments thereof thereby forming a bound ligand binder. (ii) A location of the bound ligand binder is identified on the solid support, thereby detecting the ligand binder.

Examples

Using split pool library synthesis Applicants were able to increase the number of compounds displayed by at least 1,000× over current methods. The compositions provided herein are a highly diverse collection of molecules immobilized in an extremely dense array on solid support. To prepare Applicants' system, the assembled precursor library is immobilized into a planar array. The entire immobilized array is decoded, as each library member now occupies a permanent and discrete space in a planar array, the decoding converts what was a chemically encoded library into a spatially addressed library. The chemical encoding units are removed and subsequent synthetic transformations are performed across the immobilized library, completing the library synthesis. The library can then be screened to identify molecules demonstrating useful function.

When encoded split pool synthesis is combined with established methods of high density bead immobilization and oligonucleotide sequencing, the system allows for screens of fully decoded split pool libraries on a scale that was not previously possible. By analogy to next generation sequencing technology, fully decoded screening sets of up to 108 to 1010 in a microarray format should be achievable. Provided herein are "tagless" libraries for further chemistry. By decoding prior to screening, oligonucleotide tags can be removed which accomplishes two things: (i) additional chemistry that would be incompatible with the oligonucleotide tag can be done on the immobilized library (chemical incompatibility is one of the stated challenges of encoded combinatorial chemistry); (ii) removal of the tags eliminates the potential of the tags interfering with the assays of interest. The encoding chemistry enables Applicants to harness the power of split-pool synthesis for chemical library generation, yet allows for libraries to be evaluated in relatively information rich screens, rather than selections. The relative performance of all library members in a given assay are evaluated, not just selected 'hits'. Compounds that prove problematic in one or more assays can be easily identified and flagged, reducing the number of potential false positives in subsequent screens. This facilitates the development of structure activity relationships.

The final bioactive compounds that are screened for activity are formed after decoding and removal of the tags. What is immobilized and decoded are protected, synthetic intermediates. For the invention provided herein, at least one additional chemical step is performed after decoding and removal of the nucleic acid domain to finish preparing the "bioactive agents" (this could include: deprotection, macrocyclization etc).

The potential benefits of encoding a split-pool library synthesis using nucleic acids are well known as are the synthetic challenges. Applicants' specific encoding strategy allows for the creation of screenable DNA encoded libraries in fewer linear chemical transformations per step than previously demonstrated, with each encoding step being independently decodable.

The microparticle also referred to herein as "core" could be a dendrimer, a hyperbranched polymer, a functionalized silica particle, a functionalized polymer particle. The core could be magnetic. The core could range in size from 20 nm to 200 microns in diameter. The core is functionalized with a reactive moiety that allows attachment of building blocks to make the library molecules, a different reactive moiety that allows attachment of DNA tags for encoding, and, in some cases, a third different reactive moiety which aids in covalent immobilization of the core to a surface.

The multidentate core can be a 0.9 micron magnetic polymeric bead functionalized with a surface of polyethylene glycol terminated with orthogonally protected amines.

The synthetic precursor (ligand domain including a protecting moiety) could be any product of multi-step support-bound synthesis, with the restriction that any synthetic transformations used to create the synthetic precursor, once attached to the core particle must be compatible with the core chemical structure and are either orthogonal/compatible with the described encoding chemistry or performed prior to incorporation of the first encoding tags. The synthetic precursors may be side chain protected polyamides.

The Encoding tags (nucleic acid domains) consist of unique, pre-synthesized, functionalized nucleic acid derivatives covalently linked directly to the core particle through a cleavable linker or indirectly through other encoding tags. Tag sequences are of sufficient length and composition and encode entire library. To enable decoding of specific encoded synthetic steps, independent of other encoded synthetic steps. For example: decoding the tags used to encode for the second step in a synthesis should be completely independent of the ability to decode tags used to encode the first or third steps in a synthesis. Unsuccessful incorporation of tags at step one adversely impact incorporation of tags at step two. An inability to "decode" step one will affect the ability to "decode" step two for a given encoded library member. Applicants' approach may require longer nucleic acid sequences but provides a more robust encoding/decoding process. Tags are compatible with the chosen method of decoding or sequencing. For example; if sequencing of tags is to be performed by a process of sequential hybridizations, tags should be relatively isothermal to one another and contain sufficient sequence differences such that undesired cross hybridization is minimized. If sequencing of tags is to be done through any of the enzymatic based sequencing by synthesis or sequencing by ligation approaches, tags may require common primer binding sites Tag chemical structures: (i) stable and unreactive to the synthetic transformations used to construct the precursor library; (ii) removable from the core particle after it is sequenced; (iii) compatible with method of decoding/sequencing. For example, sequencing by hybridization could be done with DNA, PNA, LNA, RNA, modified RNA, modified DNA analogues or some combinations thereof. For any enzymatic based sequencing approaches, DNA is preferred. The protected oligonucleotide structures could be used to improve chemical orthogonality, wherein protecting moietiess on the tag are removed prior to decoding. (for example, the exocyclic amines of the nucleobases may be protected prior to or immediately following tag incorporation)

Tag cleavage site structures: (i) tags may be directly attached to the core particle or indirectly to the core through other tags, all core particle attachment points for tags ultimately contain a site of cleavability. (ii) preferred cleavable structures, following cleavage, leave the core particle surface free of reactive moieties which may interfere with subsequent chemistry or assays (e.g., ester cleavage site which leave a free alcohol; trityl ether cleavage site which leave a free alcohol).

Tag linking structures: the encoding tags may be 20-mer DNA based oligonucleotides with zero C content and 25% G content. The tags differ from one another by at least a six base pair mismatch. The tags are linked to the support and or one another through 1,3 triazole linkages all ultimately connected to the core particle through a cleavable ester bond. Any method of attachment and any surface used must be compatible with the decoding conditions and microarray assay conditions, as well as tag removal conditions, and any synthetic reaction conditions applied to the array. Applicants have demonstrated immobilization on patterned quartz, patterned silicon, and carboxymethyldextran functionalized glass.

DNA tag removal: Conditions are dependent on structure at tag cleavage site. With ester linkage, Applicants have used ammonium hydroxide and methylamine. Ligand deprotection and further synthetic modifications. Applicants have removed all side chain protecting moietiess from polyamide structures. Selective side chain de-protection followed by macrolactamization will be performed. Incorporation of fluorophore-quencher pairs or solvatochromic moieties will be performed. The compositions provided herein may be useful, inter alia, for microarray screens, fluorescence, colorimetric, or electrochemical readouts binding assays in which fluorescently labeled proteins of interest are incubated over the array to identify binders has been demonstrated.

In embodiments, the prototype chips are at 2.4 micron C-C (center to center) spacing in a hexagonal array. That results in 4.99 square microns per bead (less than the 5.76 square microns per bead expected because the beads are hexagonally packed), or 20 million beads per square centimeter, or 200,000 beads per square millimeter, or ~376 million particles within the area equivalent of a standard 25 mm by 75 mm microscope slide.

In embodiments, particles have been immobilized into a 1.3 micron C-C spacing hexagonal array. That results in 1.46 square microns per bead, or 78.9 million beads per square centimeter, or 789,000 beads per square millimeter, or 1.28 billion beads within the area equivalent to a 25 mm by 75 mm microscope slide.

In embodiments, particles have been immobilized into a 1.3 micron C-C spacing square packed array. That results in 1.69 square microns per bead, or 59 million beads per square centimeter, or 591,715 beads per square millimeter, or 1.11 billion beads within the area equivalent to a 25 mm by 75 mm microscope slide.

In embodiments, an array is hexagonally packed with a density of 1 bead per square micron (C-C spacing of ~1.075 microns).

Materials and Methods

Reagents

Triethylamine (TEA), Diisopropylethylamine (DIPEA), Diisopropylcarbodiimide (DIC), dimethylaminopyridine (DMAP), dimethylformamide (DMF), dimethylsulfoxide (DMSO), Triton X-100 (TX100), azidoacetic acid (Aza), 1-[Bis(dimethylamino)methylene]-1H-1,2,3-triazolo[4,5-b]pyridinium 3-oxid hexafluorophosphate (HATU), (7-Azabenzotriazol-1-yloxy)tripyrrolidinophosphonium hexafluorophosphate (PYAOP), Tris(3-hydroxypropyltriazolylmethyl)amine (THPTA), Copper(I) bromide dimethyl sulfide complex (CuBrDMS), Boc-Glycine, and Fmoc-Glycine were purchased from Sigma-Aldrich and used as received. All other Fmoc protected amino acids were purchased from Novabiochem or Advanced Chemtech. Water used in all wash and reaction buffers was obtained from a Millipore MilliQ purification system. Peg reagents used for the initial microparticle functionalization were purchased from Rapp Polymere or Quanta Biodesign. Promag Beads are provided by Bangs Laboratories as a 2.6% w/v solution in water and have the following characteristics: 880 nm average diameter. Composed of iron oxide embedded within a highly crosslinked polymer matrix. Surface of the particles displays free carboxylic acid reactive moieties at 440 nmole equivalents per milligram. Approximately 2 billion microparticles are contained within one milligram of the stock particles. All nucleic acid tags and fluorescently labeled complement sequences were purchased from IDT.

TABLE 1

| Oligo sequence name | IDT Sequence code | SEQ ID NO: |
|---|---|---|
| Tag $A_0$ | /5Hexynyl/AAC CAC ACA CAC ACA ACC /3AmMO/ | 1 |
| Tag $A_1$ | /5Hexynyl/AAC CAC ACA CAC CAA ACC /3AmMO/ | 2 |
| Tag $B_2$ | /5Hexynyl/ACG AAC ACA CAC GTA CGA /3AmMO/ | 3 |
| Tag $C_2$ | /5Hexynyl/CAA GAC ACA CAC GTC AAG /3AmMO/ | 4 |
| Tag $D_2$ | /5Hexynyl/CCT TAC ACA CAC GTC CTT /3AmMO/ | 5 |
| Tag $B_3$ | /5Hexynyl/ACG AAC ACA CAC TGA CGA /3AmMO/ | 6 |
| Tag $C_3$ | /5Hexynyl/CAA GAC ACA CAC TGC AAG /3AmMO/ | 7 |
| Tag $D_3$ | /5Hexynyl/CCT TAC ACA CAC TGC CTT /3AmMO/ | 8 |
| Anti-$B_2$-Cy3 | /5Cy3/TCG TAC GTG TGT GTT CGT | 9 |
| Anti-$C_2$-Cy3 | /5Cy3/CTT GAC GTG TGT GTC TTG | 10 |
| Anti-$D_2$-Cy3 | /5Cy3/AAG GAC GTG TGT GTA AGG | 11 |
| Anti-$B_3$-AF647 | /5Alex647N/TCG TCA GTG TGT GTT CGT | 12 |
| Anti-$C_3$-FITC | /56-FAM/CTT GCA GTG TGT GTC TTG | 13 |
| Anti-$D_3$-FITC | /56-FAM/AAG GCA GTG TGT GTA AGG | 14 |
| Anti-$A_0$-Cy3 | /5Cy3/GGT TGT GTG TGT GTG GTT | 15 |
| Anti-$A_1$-FITC | /56-FAM/GGT TTG GTG TGT GTG GTT | 16 |

Ligand Domain Sequences

SEQ ID NO: 17:   YPYDVPDYA. (HA-tag)

SEQ ID NO: 18   EQKLISEEDL (Myc-tag)

Additional Reagent Abbreviations

DITx MilliQ water containing 1% Triton X-100

DMSOTx DMSO containing 1% Triton X-100

PBT 100 mM phosphate buffer, pH 7.0 containing 1% Triton X-100

AMA 1:1 mix of ammonium hydroxide and 30% methylamine in ethanol

General Microparticle Handling Procedures

Similar to most solid phase synthetic procedures, a typical reaction involves 1) dispersing the microparticles in a reaction solution 2) adding additional solvents or reagents as needed for the reaction 3) providing occasional or constant agitation at some specified reaction temperature for some period of time and 4) following the reaction, the reagents and soluble byproducts of the reaction are separated from the microparticles through a series of washes. The separation and washing steps for Applicants' microparticles consists of multiple rounds of 1) magnetically assisted pelleting of the microparticles and aspiration of the supernatant followed by 2) resuspension of the microparticle pellet in a suitable wash solution.

ProMag Microparticle Functionalization
Initial PEGylation:

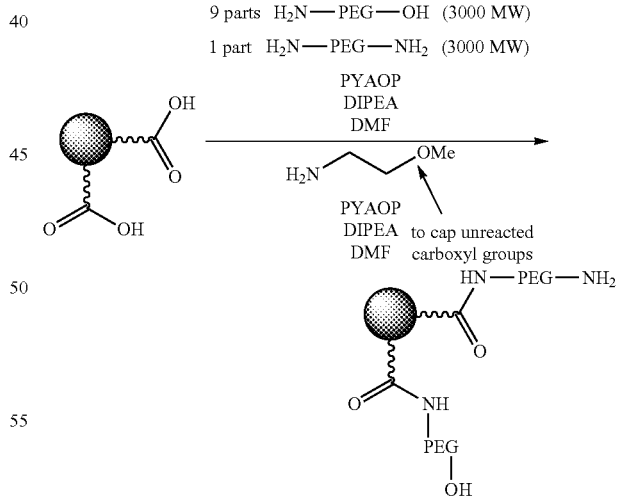

Large-scale functionalization to create pegylated beads (with a 4.5:1 ratio of hydroxyl groups to amine groups) are done in order to eliminate any batch-to-batch variations. 250 uL of stock ProMag beads are washed with DMFTx (1 mL, x3) and suspended in 150 uL DMFTx. Amino hydroxy PEG 3000 (270 mg) and bis amine PEG 3000 (30 mg) are weighed into a 1.5 mL conical tube and melted in an oil bath at 65 C. The beads are added to the melted PEG and mixed thoroughly/heated. Fifty five microliters of DIPEA is added to the reaction mix and vortexed followed by the addition of solid PyAOP (160 mg). The reaction ran at 65 C for 45 minutes while heating with an oil bath. The final concentrations in the reaction end up being (200 mM PEG, 600 mM PyAOP, 600 mM DIPEA). After 45 minutes the remaining carboxylic acids on the surface are capped with 2-methoxyethyl amine (250 uL), let incubate at the same temperature for 10 minutes then wash the beads with DMFTx (1 mL, ×3), then resuspend with 250 uL DMFTx. A 50 uL aliquot taken out and washed with MilliQ water (400 uL, ×3) and loaded on the burned off clean/tared pan, put in the oven at 95 C and the following method was ran. Jump to 95 C, isotherm for 10 min, ramp 20 C/min until 500 C, isotherm for 30 minutes. [Starting mass: 1.5940 mg. At 100 C 98.86%. At 500 C 31.30%] This corresponds to 25.4% added functionality, comparison to the last large batch which was 24.3% added functionalization (1.704 mg, 99.81% at 100 C and 32.08% at 500 C) as compared to the first two Large batches prepared by the same protocol which had an added funct of 25.6%.

BOC Protection (×2)

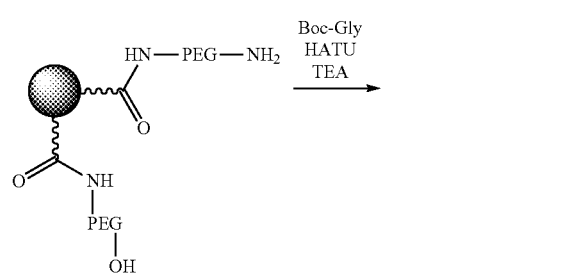

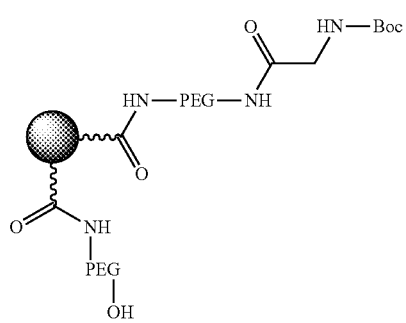

The rest of the beads are Boc protected by washing into DMSOTx (1 mL, ×3), suspending in 170 uL DMFTx, adding 14 mg Boc-Gly OH, followed by 22.3 uL TEA, and 30.4 mg HATU, in that order. The reaction ran at 65 C for 30 min in an oil bath, after which the beads were washed with DMFTx (500 mL, ×3) and subject to the same conditions one more time. The beads were then subject to AMA (200 uL, 65 C, 5 min) then washed into DMFTx at stock concentration.

DIC/DMAP with Long Chain Azide (×3)

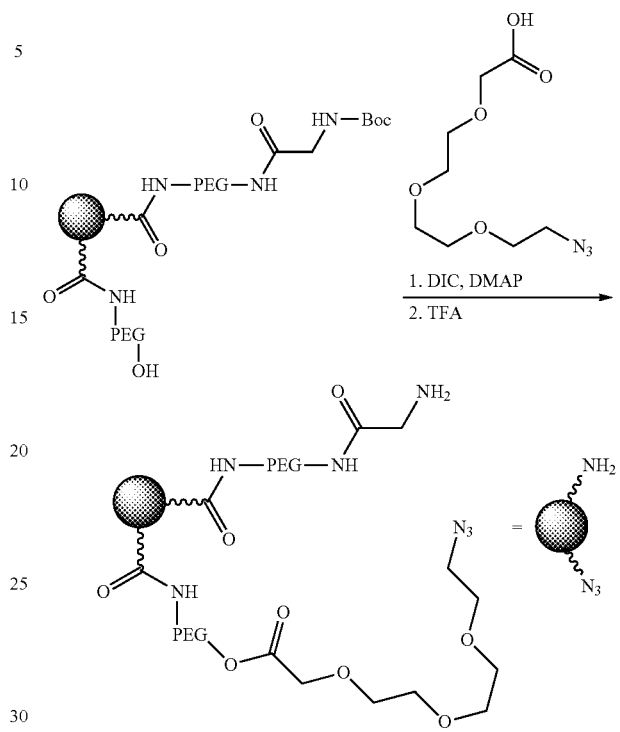

Beads are resuspended in 400 uL DMFTx, to this is added 80 uL of 500 mM long chain azido acid (11.66 mg/100 uL), followed by 6.7 uL DIC, then 10 uL of DMAP (80 mg/ml stock in DMF). These coupling conditions were repeated a total of three times—washing with DMFTx (200 uL, ×3) in between. The Boc group is then removed by treatment with TFA for 15 minutes. This large batch is then washed into PBT (400 uL, ×3) and suspended in 400 uL (×4 dilution from stock). Protocol for attaching azido acetic acid in a alkali cleavable form (connected to the microparticle through an ester bond) is performed in a similar fashion.

Standard HATU Amino Acid Coupling Conditions 400 mM HATU, 400 mM FMOC'ed amino acid, 800 mM TEA in 10% DITx, 90% DMSOTx, 65 C, 30 minutes Beads are washed into DITx (100 uL, ×3), and suspended in 10 uL DITx. To this is added the FMOC'ed amino acid in 80 uL DMSOTx (400 mM for a 200 uL rxn volume), followed by TEA (10 uL, 101.19 g/mole, 0.726 g/mL), and lastly HATU (15 mg, 380.23 g/mole) is added last as a solid and the tube is set on the red heat block set at 65 C for 30 minutes. Double couplings are done (without washing in between) with all amino acids to ensure 100% conversion.

Standard HATU coupling of azide to the amine reactive moiety on the nucleic acid tags 400 mM HATU, 400 mM 2-azidoacetic acid, 800 mM TEA in 10% DITx, 90% DMSOTx, 65 C, 30 minutes Beads are washed into PBT (100 uL, ×3), and suspended in 10 uL DITx. To this is added DMSOTx (80 uL), followed by 2-azidoacetic acid (3 uL, 101.06 g/mole, 1.35 g/mL), followed by TEA (22.3 uL, 101.19 g/mole, 0.726 g/mL), and lastly HATU (15 mg, 380.23 g/mole) is added last as a solid and the tube is set on the red heat block set at 65 C for 30 minutes. Double couplings are done (without washing in between) with all acids to ensure 100% conversion.

Copper Catalyzed Azide Alkyne (Huisgen) Cycloaddtion Conditions (Encoding Step)

Catalyst stock solution preparation: Cu(I)Br DMS (205.58 g/mole) had previously been weighed out in the glovebox in 20 mL scintillation vials. DMSO (that is kept in the glovebox) is added to the vial such that a concentration of 4.5 mg/mL (22 mM) is achieved. THPTA (tris(3-hydroxy-propyltriazolylmethyl)amine) (434.5 g/mole) is weighed out outside of the hood and dissolved to a concentration of 2.8 mg/125 uL (52 mM). The Cu (I) and the ligand solutions are combined in a 1:2 v:v ration of Cu(I) to ligand giving the following concentrations: 35 mM THPTA and 7.3 mM Cu(I)Br DMS in 50% DMSO and 50% MilliQ water.

The beads are washed into PBT (100 uL, ×3) and suspended in 13 uL PBT. To this is added 10 uL oligo tag (from 500 uM stock solution). This is transferred into the glovebox with a minimum of 4 pump/purge cycles. Two microliters of the catalyst stock solution is added and the PCR tube is set on the PCR block set to 60 C for 30 minutes, after which the reaction is quenched with 500 mM EDTA (outside of the glove box) by added 100 uL EDTA and incubating for 3 minutes before washing with PBT (200 uL, ×5).

Standard FMOC Deprotection Conditions 100 uL 20% piperadine in DMFTx for 10 minutes at rt (×3).

Competitive Hybridization Conditions, example using for distinguishing between tags A0 and A1

Anti-A0-Cy3, and Anti-A1-FITC are purchased from IDT and diluted to stocks of 500 μM in MilliQ water. A hybridization solution that is to be applied to bead samples is prepared as follows. 404, of formamide, 20 μL of 20×SSPE buffer (Sigma), 10 μL of DITx, 20 μL of DI, 5 μL of Anti-A0-Cy3 stock, and 5 μL of Anti-A1-FITC stock are mixed in a single PCR tube, and stored in the dark till use.

Samples of beads (1.6 μg) displaying A0 or A1 on their respective surfaces were placed in separate PCR tube, pelleted, and the supernatant was removed by vacuum aspiration. Each bead pellet was immediately suspended in 25 μL of hybridization solution. The bead slurry mixtures were allowed to hybridize over the next 15 minutes at room temperature, away from light. After the indicated time period, the bead samples were pelleted, the hybridization solution was removed by vacuum aspiration. Beads were then washed 3× with 25 μL of PBT, and finally suspended in 25 μL pf PBT. 5 μL of this bead sample is removed, placed in a 1356 well plate and imaged at the microscopy core using a Zeiss Observer, 63× water objective, 1.6 optovar in the brightfeild, DsRed and EGFP channels. An extra 5 μL sample of each bead type was loaded in a separate well of the plate and used to set the exposure times for the DsRed and EGFP by the 2014 Zeiss ZenBlue software. The additional A0 sample was used to set the DsRed and the additional A1 sample was used to set the EGFP. After setting the exposure time the unexposed A0 and A1 samples were imaged using the same, fixed exposure times.

EMBODIMENTS

Embodiment 1

A microparticle covalently attached to: (i) a ligand domain through a first linker; and (ii) a nucleic acid domain through a second linker, wherein said second linker is cleavable and said first linker is not cleavable under a condition that said second linker is cleavable.

Embodiment 2

The microparticle of embodiment 1, wherein said ligand domain comprises a protecting moiety attached to a reactive moiety.

Embodiment 3

The microparticle of embodiment 2, wherein said protecting moiety comprises an amino acid side chain.

Embodiment 4

The microparticle of embodiment 2, wherein said protecting moiety comprises an amino terminus or a carboxy terminus.

Embodiment 5

The microparticle of embodiment 1, wherein said microparticle is a microbead.

Embodiment 6

The microparticle of embodiment 1, wherein said microparticle is a functionalized microbead.

Embodiment 7

The microparticle of embodiment 1, wherein said microparticle is a magnetic microbead.

Embodiment 8

The microparticle of embodiment 1, wherein said microparticle is a metallic microbead.

Embodiment 9

The microparticle of embodiment 1, wherein said microparticle is a silica microbead.

Embodiment 10

The microparticle of embodiment 1, wherein said microparticle is a polymeric microbead.

Embodiment 11

The microparticle of embodiment 1, wherein said microparticle a dendrimer.

Embodiment 12

The microparticle of embodiment 1, wherein said microparticle is a branched polymer.

Embodiment 13

The microparticle of any one of embodiments 1-12, wherein said second linker is a photocleavable linker.

Embodiment 14

The microparticle of any one of embodiments 1-12, wherein said second linker is an acid labile linker.

Embodiment 15

The microparticle of any one of embodiments 1-12, wherein said second linker is an alkali labile linker.

Embodiment 16

The microparticle of any one of embodiments 1-15, wherein said ligand domain is a peptide.

Embodiment 17

The microparticle of any one of embodiments 1-15, wherein said ligand domain is a small molecule.

Embodiment 18

The microparticle of any one of embodiments 1-15, wherein said ligand domain is a protein.

Embodiment 19

The microparticle of embodiment 16, wherein said ligand domain binds to a ligand binder.

Embodiment 20

The microparticle of embodiment 19, wherein said ligand binder is a biomolecule.

Embodiment 21

The microparticle of embodiment 20, wherein said biomolecule is a nucleic acid.

Embodiment 22

The microparticle of embodiment 20, wherein said biomolecule is a protein.

Embodiment 23

The microparticle of any one of embodiments 1-16, wherein said ligand domain is not bound to a ligand binder.

Embodiment 24

The microparticle of any one of embodiments 1-23, wherein said ligand domain is a plurality of ligand domains attached through a plurality of first linkers.

Embodiment 25

The microparticle of any one of embodiments 1-24, wherein said nucleic acid domain is a plurality of nucleic acid domains attached through a plurality of second linkers.

Embodiment 26

The microparticle of any one of embodiments 1-25, wherein said microparticle is attached to a solid support.

Embodiment 27

The microparticle of embodiment 26, wherein said solid support is a planar support.

Embodiment 28

The microparticle of embodiment 26 or 27, wherein said microparticle is connected through a third linker to said solid support.

Embodiment 29

The microparticle of embodiment 26 or 27, wherein said microparticle is non-covalently attached to said solid support.

Embodiment 30

The microparticle of embodiment 26 or 27, wherein said microparticle is mechanically attached to said solid support.

Embodiment 31

The microparticle of any one of embodiments 26-30, wherein a plurality of microparticles are attached to said solid support.

Embodiment 32

The microparticle of embodiment 31, wherein said plurality of microparticles form a disordered array.

Embodiment 33

The microparticle of embodiment 31, wherein said plurality of microparticles form an ordered array.

Embodiment 34

The microparticle of embodiment 31, wherein said the plurality of microparticles form an hexagonal array.

Embodiment 35

The microparticle of embodiment 31, wherein said the plurality of microparticles form a square packed array.

Embodiment 36

The microparticle of any one of embodiments 32-35, wherein said array includes at least about 200,000 microparticles per square millimeter.

Embodiment 37

The microparticle of any one of embodiments 32-35, wherein said array includes about 200,000 microparticles per square millimeter.

Embodiment 38

The microparticle of any one of embodiments 32-35, wherein said array includes 789,000 microparticles per square millimeter.

Embodiment 39

The microparticle of any one of embodiments 32-35, wherein said array includes 591,715 microparticles per square millimeter.

Embodiment 40

The microparticle of any one of embodiments 31-35, wherein at least about $10^6$ of said microparticles are attached to said solid support.

Embodiment 41

The microparticle of embodiment 40, wherein each of said microparticles is different.

Embodiment 42

The microparticle of embodiment 40, wherein about $10^6$ to $10^9$ of said microparticles are attached to said solid support.

Embodiment 43

The microparticle of embodiment 42, wherein about $10^9$ of said microparticles are attached to said solid support.

Embodiment 44

The microparticle of any one of embodiments 31-43, wherein said solid support comprises a plurality of wells each of said wells capturing one of said microparticle.

Embodiment 45

The microparticle of any one of embodiments 1-44, wherein said nucleic acid domain comprises a nucleic acid sequence.

Embodiment 46

The microparticle of embodiment 45, wherein said nucleic acid sequence is bound to a complementary nucleic acid sequence.

Embodiment 47

The microparticle of embodiment 46, wherein said complementary nucleic acid sequence comprises a detectable moiety.

Embodiment 48

The microparticle of embodiment 47, wherein said detectable moiety is a fluorescent moiety.

Embodiment 49

A solid support attached to a microparticle, wherein said microparticle is covalently attached to: (i) a ligand domain through a first linker; and (ii) a cleaved linker moiety.

Embodiment 50

The microparticle of embodiment 49, wherein said ligand domain comprises a protecting moiety attached to a reacting group.

Embodiment 51

The microparticle of embodiment 49, wherein said ligand domain is bound to a ligand binder.

Embodiment 52

The microparticle of embodiment 49 or 51, wherein said cleaved linker moiety is a remnant of a cleavable linker.

Embodiment 53

The microparticle of embodiment 52, wherein said ligand domain is a plurality of ligand domains attached through a plurality of first linkers.

Embodiment 54

The microparticle of embodiment 53, wherein said cleaved linker moiety is a plurality of cleaved linker moieties.

Embodiment 55

The microparticle of any one of embodiments 49-54, wherein said solid support is a planar support.

Embodiment 56

The microparticle of any one of embodiments 49-55, wherein said microparticle is non-covalently attached to said solid support.

Embodiment 57

The microparticle of any one of embodiments 49-55, wherein said microparticle is connected through a third linker to said solid support.

Embodiment 58

The microparticle of any one of embodiments 49-55, wherein said microparticle is mechanically attached to said solid support.

Embodiment 59

The microparticle of any one of embodiments 49-58, wherein a plurality of microparticles are attached to said solid support.

Embodiment 60

The microparticle of embodiment 59, wherein said plurality of microparticles form a disordered array.

Embodiment 61

The microparticle of embodiment 59, wherein said plurality of microparticles form an ordered array.

Embodiment 62

The microparticle of any one of embodiments 59-62, wherein at least about $10^6$ of said microparticles are attached to said solid support and wherein each of said microparticles is different.

Embodiment 63

The microparticle of embodiment 62, wherein about $10^6$ to $10^9$ of said microparticles are attached to said solid support.

Embodiment 64

The microparticle of embodiment 63, wherein about $10^9$ of said microparticles are attached to said solid support.

Embodiment 65

The microparticle of any one of embodiments 59-64, wherein said solid support is within a detection device.

Embodiment 66

The microparticle of embodiment 65, wherein said detection device detects said ligand binder bound to said ligand domain and identifies a location of said bound ligand binder on said solid support.

Embodiment 67

A method of forming a cleaved microparticle, said method comprising:
(i) attaching a microparticle of any one of embodiments 1-25 to a solid support, thereby forming an immobilized microparticle;
(ii) cleaving said second linker of said immobilized microparticle, thereby forming a cleaved microparticle.

Embodiment 68

The method of embodiment 67, further comprising prior to said cleaving of step (ii) and after said attaching of step (i), binding a complementary nucleic acid sequence to said nucleic acid domain.

Embodiment 69

The method of embodiment 67 or 68, wherein said cleaving comprises contacting said immobilized microparticle with a cleaving agent.

Embodiment 70

The method of embodiment 69, wherein said cleaving agent is an acid.

Embodiment 71

The method of embodiment 70, wherein said cleaving agent is trifluoroacetic acid.

Embodiment 72

The method of embodiment 67 or 68, wherein said cleaving does not comprise cleaving said first linker.

Embodiment 73

The method of embodiment 69, wherein said cleaving agent is an alkali agent.

Embodiment 74

A method of detecting a ligand binder, said method comprising: (i) attaching a microparticle of any one of embodiments 1-25 to a solid support, thereby forming an immobilized microparticle; (ii) binding a complementary nucleic acid to said nucleic acid domain of said immobilized microparticle and determining a location of said nucleic acid domain on said solid support, thereby forming a decoded and mapped microparticle; (iii) cleaving said second linker of said decoded and mapped microparticle, thereby forming a mapped and cleaved microparticle; (iv) binding a ligand binder to said ligand domain of said mapped and cleaved microparticle; and (v) identifying a location of said bound ligand binder on said solid support, thereby detecting said ligand binder.

Embodiment 75

A method of detecting a ligand binder, said method comprising: (i) contacting a ligand binder with a microparticle of any one of embodiments 49-58; thereby forming a bound ligand binder; and (ii) identifying a location of said bound ligand binder on said solid support, thereby detecting said ligand binder.

What is claimed is:

1. A microparticle immobilized on a solid support, wherein said microparticle is covalently attached to:
   (i) a ligand domain through a first linker; and
   (ii) a nucleic acid domain through a second linker,
   wherein said nucleic acid domain identifies said ligand domain;
   wherein said second linker comprises an acyl group, a sulfonamide group, or a photocleavable group; and
   wherein said second linker is cleavable under a condition that does not cleave said first linker.

2. The microparticle of claim 1, wherein said ligand domain comprises a removable protecting moiety covalently attached to a reactive moiety.

3. The microparticle of claim 2, wherein said removable protecting moiety comprises an amino acid side chain, an amino terminus, or a carboxy terminus.

4. The microparticle of claim 1, wherein said ligand domain is selected from the group consisting of a peptide, a small molecule, and a protein.

5. The microparticle of claim 1, wherein said ligand domain is bound to a ligand binder.

6. The microparticle of claim 1, wherein said ligand domain comprises a plurality of ligand domains attached through a plurality of first linkers.

7. The microparticle of claim 1, wherein said nucleic acid domain comprises a plurality of nucleic acid domains attached through a plurality of second linkers.

8. The microparticle of claim 1, wherein said nucleic acid domain is bound to a detectably labeled complementary nucleic acid sequence.

9. A solid support comprising a plurality of wells, wherein each of said plurality of wells further comprises an immobilized microparticle, thereby forming an ordered array, wherein each of said immobilized microparticles is covalently attached to:
   (i) a ligand domain through a first linker; and
   (ii) a nucleic acid domain through a second linker;
   wherein said nucleic acid domain identifies said ligand domain;

wherein said second linker comprises an acyl group, a sulfonamide group, or a photocleavable group; and
wherein said second linker is cleavable under a condition that does not cleave said first linker.

10. The solid support of claim 9, wherein said ligand domain comprises a removable protecting moiety attached to a reactive moiety.

11. The solid support of claim 9, wherein said ligand domain is bound to a ligand binder.

12. The solid support of claim 9, wherein said ligand domain is selected from the group consisting of a peptide, a small molecule, and a protein.

13. The solid support of claim 11, wherein said solid support is within a detection device, wherein said detection device detects said ligand binder bound to said ligand domain and identifies a location of said bound ligand binder on said solid support.

14. The microparticle of claim 1, wherein said microparticle is selected from the group consisting of a functionalized microbead, a magnetic microbead, a metallic microbead, a polymeric microbead, a silica microbead, a dendrimer, and a branched polymer.

15. The microparticle of claim 2, wherein said removable protecting moiety is selected from the group consisting of fluorenylmethyloxycarbonyl, tert-butyl, and carboxybenzyl.

16. The microparticle of claim 2, wherein said reactive moiety is selected from the group consisting of a carboxylic acid, an amine, a thiol, or an alcohol.

17. The solid support of claim 9, wherein said second linker is a photocleavable linker, an acid labile linker, or an alkali labile linker.

18. The solid support of claim 9, wherein said nucleic acid domain is bound to a detectably labeled complementary nucleic acid sequence.

19. The solid support of claim 9, wherein said ordered array includes at least 10,000 microparticles per square millimeter.

20. The solid support of claim 9, wherein said condition is selected from the group consisting of UV irradiation, light irradiation, trifluoroacetic acid, ammonium hydroxide, ammonia, methylamine, and a mixture of ammonium hydroxide and methylamine.

* * * * *